United States Patent
Figura et al.

(10) Patent No.: US 9,867,768 B2
(45) Date of Patent: *Jan. 16, 2018

(54) FOAMING PERFORMANCE IN CLEANSING COMPOSITIONS THROUGH THE USE OF NONIONIC, AMPHIPHILIC POLYMERS

(71) Applicant: Lubrizol Advanced Materials, Inc., Cleveland, OH (US)

(72) Inventors: Brian D. Figura, Cleveland, OH (US); Wei-Yeih Yang, Brecksville, OH (US); Krishnan Chari, Hudson, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/771,915

(22) PCT Filed: Mar. 6, 2014

(86) PCT No.: PCT/US2014/020982
§ 371 (c)(1),
(2) Date: Sep. 1, 2015

(87) PCT Pub. No.: WO2014/138327
PCT Pub. Date: Sep. 12, 2014

(65) Prior Publication Data
US 2016/0022566 A1    Jan. 28, 2016

Related U.S. Application Data

(60) Provisional application No. 61/774,868, filed on Mar. 8, 2013.

(51) Int. Cl.
| | |
|---|---|
| *A61K 8/81* | (2006.01) |
| *A61Q 5/02* | (2006.01) |
| *C11D 1/02* | (2006.01) |
| *A61Q 5/12* | (2006.01) |
| *C11D 3/00* | (2006.01) |
| *C11D 3/37* | (2006.01) |
| *A61K 8/86* | (2006.01) |
| *A61K 8/89* | (2006.01) |
| *A61K 8/898* | (2006.01) |

(52) U.S. Cl.
CPC .............. *A61K 8/8182* (2013.01); *A61K 8/86* (2013.01); *A61K 8/89* (2013.01); *A61K 8/898* (2013.01); *A61Q 5/02* (2013.01); *A61Q 5/12* (2013.01); *C11D 3/0094* (2013.01); *C11D 3/3746* (2013.01); *A61K 2800/54* (2013.01)

(58) Field of Classification Search
CPC ... A61K 8/81; A61Q 5/02; C11D 1/02; C11D 3/3707; C11D 3/3715; C11D 3/3719
See application file for complete search history.

(56) References Cited

U.S. PATENT DOCUMENTS

| | | |
|---|---|---|
| 3,480,546 A | 11/1969 | Bashaw et al. |
| 9,433,571 B2 * | 9/2016 | Figura .................. C11D 3/0005 |
| 2009/0074695 A1 | 3/2009 | Mahe et al. |
| 2009/0074696 A1 | 3/2009 | Biganska et al. |

FOREIGN PATENT DOCUMENTS

JP     2008150359 A     7/2008

* cited by examiner

*Primary Examiner* — Brian P Mruk
(74) *Attorney, Agent, or Firm* — Thoburn T. Dunlap

(57) ABSTRACT

The invention relates to a method for improving the foaming and/or yield value properties associated with surfactant containing compositions comprising at least one anionic surfactant, the method comprises combining an effective amount of at least one nonionic, amphiphilic polymer with at least one anionic detersive surfactant in combination with an optional surfactant selected from amphoteric surfactants, nonionic surfactants and combinations of two or more thereof. The at least one nonionic amphiphilic polymer is prepared from a free radically polymerizable monomer composition comprising at least one hydrophilic monomer and at least one hydrophobic monomer, wherein said hydrophilic monomer is selected from a N-vinyl lactam and wherein said hydrophobic monomer is selected from a vinyl ester of a $C_1$-$C_{22}$ carboxylic acid or at least one monomer selected from a $C_8$-$C_{22}$ alkyl (meth)acrylate an associative monomer, a semi-hydrophobic monomer, or mixtures thereof, and an optional crosslinking monomer.

61 Claims, No Drawings

FOAMING PERFORMANCE IN CLEANSING COMPOSITIONS THROUGH THE USE OF NONIONIC, AMPHIPHILIC POLYMERS

CROSS REFERENCE TO RELATED APPLICATION

This application claims priority from PCT Application Serial No. PCT/US2014/020982 filed on Mar. 6, 2014, which claims the benefit of U.S. Provisional Application No. 61/774,868 filed on Mar. 8, 2013.

FIELD OF THE INVENTION

The present invention relates to surfactant containing cleansing compositions with improved foaming performance. In one aspect, the invention relates to a method for enhancing the foaming properties of thickened cleansing compositions having reduced levels of surfactants. The cleansing compositions comprise water, at least one anionic detersive surfactant, and at least one nonionic polymer that enhances the foaming performance of the composition.

BACKGROUND OF THE INVENTION

Surfactants are widely used in aqueous based personal care, household care and industrial and institutional care formulations as wetting agents, detergents, and emulsifiers. In personal care cleansing products (e.g., shampoos, body washes, facial cleansers, liquid hand soaps, etc.), household care cleaning products (e.g., hard surface cleaners, laundry detergents, dish soaps, automatic dish washer detergents, shower cleansers, bathroom cleansers, car wash detergents, etc.) and industrial and institutional care cleaners (high strength cleaners, detergents, etc.) the surfactant chassis is the most important component in these detersive formulations.

Although in principle any surfactant class (e.g., cationic, anionic, nonionic, amphoteric) is suitable in cleansing or cleaning applications, in practice most personal care cleansers and household cleaning products are formulated with anionic surfactants or with a combination of an anionic surfactant as the primary detersive agent with one or more secondary surfactants selected from the other surfactant classes. Anionic surfactants are often used as detersive agents in cleansers and cleaning products because of their excellent cleaning and foaming properties. From the consumer's perspective, the amount and stability of the foam directly relates to the perceived cleaning efficiency of the composition. Generally speaking, the larger the volume of foam produced and the more stable the foam, the more efficient is the perceived cleaning action of the composition. This presents a potential problem in low-surfactant formulations, as foam volume tends to decrease with decreasing surfactant concentration. Exemplary anionic surfactants traditionally utilized in these formulations include alkyl sulfates, alpha-olefin sulfonates, and alkyl benzene sulfonates. In order to provide high quality lather or foam, conventional skin cleansing products typically contain from greater than 10 wt. % to about 25 wt. % (based on the weight of the total composition) of a surfactant chassis, including relatively high levels of anionic surfactants. While the anionic surfactants and in particular the anionic sulfates and sulfonates are efficient detersive agents and produce large foam volume with good foam stability properties, they tend to be harsh to the skin and eyes. Cleansing compositions containing higher levels of surfactant tend to be harsher in terms of irritation to the eyes and skin. The high levels of surfactants used in these products tend to dehydrate and remove lipids from the skin. The surfactants act to emulsify the natural oils in the skin, which are washed away when the cleansing composition is rinsed off.

It is known that the irritation caused by anionic sulfates can be reduced by ethoxylation. However, the use of ethoxylated anionic surfactants is accompanied by a corresponding reduction in foam volume. For example, sodium lauryl sulfate, a high foaming surfactant, provides good lather but may be harsh. In contrast, sodium lauryl ether sulfate (the corresponding ethoxylate) mitigates harshness, but at typical ethoxylation levels, e.g., ethoxylated with 3 to 12 ethylene oxide units, is a poor foaming agent (see Schoenberg, "Baby Shampoo," Household & Personal Products Industry 60 (September 1979); U.S. Pat. No. 4,132,678; and U.S. Pat. Appln. Pub. 2009/0155383). Additional attempts to attenuate the harsh effects of anionic surfactants have been made by replacing some of the foam generating anionic surfactant with very mild secondary surfactants. The anionic surfactant is utilized in conjunction with a nonionic and/or an amphoteric surfactant as disclosed in U.S. Pat. No. 4,726,915. Other efforts have focused on reducing the amount of the overall surfactant level in response to the perceived negative impact of surfactants on the environment. However, reducing the relative amount of anionic surfactant in a cleansing or cleaning composition adversely affects the foaming properties of the composition.

Another attribute that consumers expect of their cleansing products is an aesthetically pleasing viscosity. Formulations that flow with a watery consistency are aesthetically unpopular to consumers with expectations of rich and creamy products. While low viscosity products may be effective for their intended purpose, they are perceived to be of low quality by the consumer. Formulations that flow with a watery consistency run off when applied to the hair and skin. For a cosmetic cleansing composition to be effective, it often must have substantivity. Rheology modifying thickeners provide this substantivity.

Rheology modifiers are used in aqueous cleansing products, such as, for example, shampoos, body washes, facial cleansers, and liquid hand soaps, to increase the viscosity to make them easier for the user to handle and/or to increase the yield stress of the composition. While a certain rheology modifier may thicken or enhance the viscosity of a composition in which it is included, it does not necessarily have desirable yield stress properties. A desirable yield stress property is critical to achieving certain physical and aesthetic characteristics in a liquid medium, such as the indefinite suspension of particles, insoluble liquid droplets, or the stabilization of gas bubbles within a liquid medium. Particles dispersed in a liquid medium will remain suspended if the yield stress (yield value) of the medium is sufficient to overcome the effect of gravity or buoyancy on those particles. Insoluble liquid droplets can be prevented from rising and coalescing and gas bubbles can be suspended and uniformly distributed in a liquid medium using yield value as a formulating tool. A yield stress fluid is used generally to adjust or modify the rheological properties of aqueous compositions. Such properties include, without limitation, viscosity improvement, flow rate improvement, stability to viscosity change over time, and the ability to suspend particles for indefinite periods of time.

Rheology modifiers prepared from homopolymers and copolymers of acrylic acid have been utilized to provide rheological properties including thickening and the suspension of particles and droplets in surfactant containing compositions. Homopolymers of acrylic acid crosslinked with an allyl ether of pentaerythritol, an allyl ether of sucrose, or an allyl ether of propylene (INCI Name: Carbomer) have been utilized as rheology modifying and suspending agents in shampoo compositions comprising an anionic detersive surfactants as disclosed in U.S. Pat. Nos. 8,153,572; 8,298,519; and 8,349,301. While these polymers provide good rheological properties, there is a need to enhance foaming properties in the cleansing compositions in which they are included.

Recently hydrophobically modified, crosslinked copolymers of acrylic acid have been proposed for use with anionic surfactant containing cleansing compositions to mitigate the adverse effects of harsh surfactants while maintaining high cleansing and foaming properties. In International Pat. Appln. Pub. No. WO 2005/023870 it is disclosed that certain hydrophobically modified materials capable of binding surfactant can be combined with anionic surfactants to produce personal care compositions that exhibit relatively low ocular and/or dermal irritation while maintaining relatively high foaming and foam stability properties. Disclosed hydrophobically modified materials include hydrophobically modified crosslinked acrylic copolymers that are synthesized from at least one ethylenically unsaturated carboxylic acid monomer and at least one ethylenically unsaturated hydrophobically modified monomer. The disclosure states that exemplary hydrophobically modified acrylic polymers are set forth in U.S. Pat. No. 6,433,061 to Noveon, Inc. The WO 2005/023870 disclosure additionally exemplifies polymers available under the trade names Carbopol® Aqua SF-1 and Carbopol® ETD 2020 both provided by Noveon Consumer Specialties of Lubrizol Advanced Materials, Inc. as suitable polymers for use as a surfactant binder.

The polymers disclosed in U.S. Pat. No. 6,433,061 as well as the polymers identified under the Carbopol® Aqua SF-1 and ETD 2020 trade names are crosslinked. At column 5, line 32 of the '061 patent it is disclosed that the "The copolymer of the present invention desirably is crosslinked by a crosslinking monomer." Moreover, all of the polymers exemplified in the '061 patent disclosure contain a crosslinking monomer. In the trade literature Carbopol® Aqua SF-1 polymer is described in Noveon Consumer Specialties of Lubrizol Advanced Materials, Inc. Technical Data Sheet TDS-294 (July, 2003) as: " . . . a lightly crosslinked acrylic polymer dispersion designed to impart suspending, stabilizing, and thickening properties to a variety of surfactant-based personal cleansing products;" and Carbopol® ETD 2020 polymer is described in Noveon Consumer Specialties of Lubrizol Advanced Materials, Inc. Technical Data Sheet TDS-187 (January, 2002) as: " . . . an 'easy to disperse' crosslinked polyacrylic acid copolymer processed in a toxicologically-preferred co-solvent system." The foregoing acrylic based crosslinked polymers are non-linear, branched polymer chains which interconnect to form three dimensional network structures and have long been used in personal care applications for their rheological and structure building properties. Upon neutralization, these anionic water soluble or dispersible polymers possess the unique ability to greatly increase the viscosity of the liquid in which they are dissolved or dispersed, even when present at concentrations considered to be quite low.

U.S. Pat. No. 8,293,845 and U.S. Pat. Appln. Pub. No. 2012/0157366 describe the use of low molecular weight linear (non-crosslinked) acrylic acid polymers and copolymers in cleansing compositions formulated with anionic surfactant containing cleansing compositions to mitigate the adverse effects of harsh surfactants while retaining foaming properties without substantially affecting the rheological properties the composition. These anionic linear polymers also require neutralization with a pH adjusting agent within a relatively narrow pH range to provide optimal irritation mitigation properties. These linear polymers convey no yield stress properties to the cleansing composition in which they are contained.

There is a need for a polymer that improves foam properties and/or yield stress properties of surfactant containing compositions formulated with an anionic primary surfactant, and which imparts mildness and is not pH dependent.

SUMMARY OF THE INVENTION

The present invention provides mild cleansing and cleaning compositions and methods for increasing foaming properties in anionic surfactant containing compositions. It has been discovered that a mild cleansing composition possessing excellent detersive and foaming properties can be obtained by incorporating at least one nonionic, amphiphilic polymer into the cleansing formulation.

In one aspect, it has been discovered that linear (non-crosslinked) nonionic, amphiphilic polymers of the invention exhibit a unique and unexpected combination of properties including the ability to enhance the foaming properties of surfactant containing compositions.

In one aspect, crosslinked, nonionic, amphiphilic polymers provide improved foaming and yield stress properties to surfactant containing compositions. The efficacy of the linear (non-crosslinked) and crosslinked polymers of the invention is not dependent on maintaining a specific pH range.

In one aspect, the invention also provides mild cleansing and cleaning compositions comprising at least one nonionic amphiphilic polymer and at least one anionic primary surfactant, and at least one optional secondary surfactant detersive surfactant selected from ethoxylated anionic surfactants, amphoteric surfactants, nonionic surfactants and combinations of two or more thereof.

In another aspect, an embodiment of the invention relates to a method of increasing foam volume associated with a cleansing composition comprising at least one anionic surfactant, said method comprising combining a nonionic, amphiphilic polymer with at least one anionic detersive surfactant in optional combination with a secondary surfactant selected from at least one amphoteric surfactant, at least one nonionic surfactant, and combinations thereof.

In another aspect, the at least one nonionic, amphiphilic polymer of the invention is capable of enhancing foam production in cleansing compositions which comprise at least one anionic primary surfactant in optional combination with at least one secondary surfactant selected from at least one amphoteric surfactant, at least one nonionic surfactant, and mixtures thereof. The nonionic amphiphilic polymer is not pH dependent and can be crosslinked to provide a desired yield stress property to a given cleansing and cleaning formulation.

In another aspect, an embodiment of the invention relates to a method of increasing foaming properties associated with a thickened cleansing composition comprising at least one detersive surfactant, the method comprising combining a crosslinked, nonionic, amphiphilic polymer with at least one anionic primary surfactant, and an optional secondary surfactant selected from at least one amphoteric surfactant, at least one nonionic surfactant and combinations thereof, wherein the concentration of the crosslinked, nonionic, amphiphilic polymer is no more than 5 wt. %, and the at least one detersive surfactant is no more than 20 wt. % (all weight percentages are based on the total weight of the composition), wherein the yield stress of the composition is at least 0.1 Pa, and the efficacy of the polymer to enhance foam properties and provide yield stress is substantially independent of pH in the range of about 2 to about 14.

In another aspect, an embodiment of the invention relates to a method of increasing foaming properties associated with a thickened cleansing composition comprising at least one detersive surfactant, the method comprising combining a crosslinked, nonionic, amphiphilic polymer with at least one anionic primary surfactant, and an optional secondary surfactant selected from at least one amphoteric surfactant, at least one nonionic surfactant and combinations thereof, wherein the concentration of the crosslinked, nonionic, amphiphilic polymer is no more than 5 wt. %, and the at least one detersive surfactant is no more than 20 wt. % (all weight percentages are based on the total weight of the composition), wherein the yield stress of the composition is at least 0.1 Pa and is substantially independent of pH in the range of about 2 to about 14, and wherein the composition is able to suspend beads of a size between 0.5 and 1.5 mm where the difference in specific gravity of the beads relative to water is in the range of 0.2 to 0.5 for a period of at least 4 weeks at room temperature.

In one aspect, the nonionic, amphiphilic polymer utilized in the method of the invention is prepared from a free radically polymerizable monomer composition comprising at least one hydrophilic monomer, at least one hydrophobic monomer, and optionally, at least one crosslinking monomer containing at least two polymerizable unsaturated moieties. In one aspect, the hydrophilic monomer is selected from N-vinyl amides, hydroxy($C_1$-$C_5$)alkyl (meth)acrylates, amino group containing monomers, or mixtures thereof. In one aspect, the hydrophobic monomer is selected from vinyl ester of an aliphatic carboxylic acid containing an acyl moiety having 2 to 22 carbon atoms, esters of (meth)acrylic acid with alcohols containing 1 to 30 carbon atoms, vinyl ethers of alcohols containing 1 to 22 carbon atoms, vinyl aromatic monomers, vinyl halides, vinylidene halides, associative monomers, semi-hydrophobic monomers, or mixtures thereof.

In one aspect, the nonionic, amphiphilic polymer utilized in the method of the invention is prepared from a free radically polymerizable monomer composition comprising at least one N-vinyl amide monomer, at least one vinyl ester of an aliphatic carboxylic acid containing an acyl moiety having 2 to 22 carbon atoms, and optionally, at least one crosslinking monomer, in optional combination with at least one monomer selected from esters of (meth)acrylic acid with alcohols containing 1 to 30 carbon atoms, associative monomers, semi-hydrophobic monomers, or mixtures thereof.

The methods, polymers and compositions of the present invention may suitably comprise, consist of, or consist essentially of the components, elements, steps, and process delineations described herein. The invention illustratively disclosed herein suitably may be practiced in the absence of any element which is not specifically disclosed herein.

Unless otherwise stated, all percentages, parts, and ratios expressed herein are based upon weight of the total compositions of the present invention.

When referring to a specified monomer(s) that is incorporated into a polymer of the invention, it will be recognized that the monomer(s) will be incorporated into the polymer as a unit(s) derived from the specified monomer(s) (e.g., repeating unit).

As used herein, the term "amphiphilic polymer" means that the polymeric material has distinct hydrophilic and hydrophobic portions. "Hydrophilic" typically means a portion that interacts intramolecularly with water and other polar molecules. "Hydrophobic" typically means a portion that interacts preferentially with oils, fats or other non-polar molecules rather than aqueous media.

As used herein, the term "hydrophilic monomer" means a monomer that is substantially water soluble. "Substantially water soluble" refers to a material that is soluble in distilled (or equivalent) water, at 25° C., at a concentration of about 3.5% by weight in one aspect, and soluble at about 10% by weight in another aspect (calculated on a water plus monomer weight basis).

As used herein, the term "hydrophobic monomer" means a monomer that is substantially water insoluble. "Substantially water insoluble" refers to a material that is not soluble in distilled (or equivalent) water, at 25° C., at a concentration of about 3% by weight in one aspect, and not soluble at about 2.5% by weight in another aspect (calculated on a water plus monomer weight basis).

By "nonionic" is meant that a monomer, monomer composition or a polymer polymerized from a monomer composition is devoid of ionic or ionizable moieties ("nonionizable").

An ionizable moiety is any group that can be made ionic by neutralization with an acid or a base.

An ionic or an ionized moiety is any moiety that has been neutralized by an acid or a base.

By "substantially nonionic" is meant that the monomer, monomer composition or polymer polymerized from a monomer composition contains less than 5 wt. % in one aspect, less than 3 wt. % in another aspect, less than 1 wt. % in a further aspect, less than 0.5 wt. % in a still further aspect, less than 0.1 wt. % in an additional aspect, and less than 0.05 wt. % in a further aspect, of an ionizable and/or an ionized moiety.

The prefix "(meth)acryl" includes "acryl" as well as "methacryl". For example, the term (meth)acrylic includes both acrylic and methacrylic, and the term (meth)acrylate includes acrylate as well as methacrylate. By way of further example, the term "(meth)acrylamide" includes both acrylamide and methacrylamide.

The term "personal care products" as used herein, without limitation, includes cosmetics, toiletries, cosmeceuticals, beauty aids, insect repellents, personal hygiene and cleansing products applied to the body, including the skin, hair, scalp, and nails of humans and animals.

The term "home care products" as used herein i, without limitation, includes products employed in a domestic household for surface cleaning or maintaining sanitary conditions, such as in the kitchen and bathroom (e.g., hard surface cleaners, hand and automatic dish care, toilet bowl cleaners and disinfectants), and laundry products for fabric care and cleaning (e.g., detergents, fabric conditioners, pretreatment stain removers), and the like.

Here, as well as elsewhere in the specification and claims, individual numerical values (including carbon atom numerical values), or limits, can be combined to form additional non-disclosed and/or non-stated ranges.

While overlapping weight ranges for the various components and ingredients that can be contained in the compositions of the invention have been expressed for selected embodiments and aspects of the invention, it should be readily apparent that the specific amount of each component in the disclosed compositions will be selected from its disclosed range such that the amount of each component is adjusted such that the sum of all components in the composition will total 100 weight percent. The amounts employed will vary with the purpose and character of the desired product and can be readily determined by one skilled in the art.

The headings provided herein serve to illustrate, but not to limit the invention in any way or manner.

DESCRIPTION OF EXEMPLARY EMBODIMENTS OF THE INVENTION

Exemplary embodiments in accordance with the present invention will be described. Various modifications, adaptations or variations of the exemplary embodiments described herein may become apparent to those skilled in the art as such are disclosed. It will be understood that all such modifications, adaptations or variations that rely upon the teachings of the present invention, and through which these teachings have advanced the art, are considered to be within the scope and spirit of the present invention.

Amphiphilic Polymer

The crosslinked, nonionic, amphiphilic polymers useful in the practice of the invention are polymerized from monomer components that contain free radical polymerizable unsaturation. In one embodiment, the crosslinked, nonionic, amphiphilic polymers useful in the practice of the invention are polymerized from a monomer composition comprising at least one nonionic, hydrophilic unsaturated monomer, at least one unsaturated hydrophobic monomer, and at least one polyunsaturated crosslinking monomer.

In one embodiment, the nonionic, amphiphilic polymers can be prepared from a monomer composition typically having a hydrophilic monomer to hydrophobic monomer ratio of from about 55:45 wt. % to about 95:5 wt. % in one aspect, from about 60:40 wt. % to about 90:10 wt. % in another aspect, from about 65:35 wt. % to about 85:15 wt. % in a further aspect, and from about 70:30 to about 80:20 wt. % in a still further aspect, based on the total weight of the hydrophilic and hydrophobic monomers present. The hydrophilic monomer component can be selected from a single hydrophilic monomer or a mixture of hydrophilic monomers, and the hydrophobic monomer component can be selected from a single hydrophobic monomer or a mixture of hydrophobic monomers.

Hydrophilic Monomer

Representative hydrophilic monomers include but are not limited to open chain and cyclic N-vinyl amides (N-vinyl lactams containing 4 to 9 atoms in the lactam ring moiety), wherein the ring carbon atoms optionally can be substituted by one or more lower alkyl groups such as methyl, ethyl or propyl); amino($C_1$-$C_5$)alkyl (meth)acrylates; hydroxy($C_1$-$C_5$)alkyl (meth)acrylates; amino group containing vinyl monomers selected from (meth)acrylamide, N—($C_1$-$C_5$) alkyl(meth)acrylamides, N,N-di($C_1$-$C_5$)alkyl(meth)acrylamides, N—($C_1$-$C_5$)alkylamino($C_1$-$C_5$)alkyl(meth)acrylamides and N,N-di($C_1$-$C_5$)alkylamino($C_1$-$C_5$)alkyl(meth)acrylamides, wherein the alkyl moieties on the disubstituted amino groups can be the same or different, and wherein the alkyl moieties on the monosubstituted and disubstituted amino groups can be optionally substituted with a hydroxyl group; other monomers include vinyl alcohol; vinyl imidazole; and (meth)acrylonitrile. Mixtures of the foregoing monomers also can be utilized.

Representative open chain N-vinylamides include N-vinylformamide, N-methyl-N-vinylformamide, N-(hydroxymethyl)-N-vinylformamide, N-vinylacetamide, N-vinylmethylacetamide, N-(hydroxymethyl)-N-vinylacetamide, and mixtures thereof. Additionally, monomers containing a pendant N-vinyl lactam moiety can also be employed, e.g., N-vinyl-2-ethyl-2-pyrrolidone (meth)acrylate.

Representative cyclic N-vinylamides (also known as N-vinyl lactams) include N-vinyl-2-pyrrolidinone, N-(1-methyl vinyl) pyrrolidinone, N-vinyl-2-piperidone, N-vinyl-2-caprolactam, N-vinyl-5-methyl pyrrolidinone, N-vinyl-3,3-dimethyl pyrrolidinone, N-vinyl-5-ethyl pyrrolidinone and N-vinyl-6-methyl piperidone, and mixtures thereof.

The amino($C_1$-$C_5$)alkyl (meth)acrylates and hydroxy($C_1$-$C_5$)alkyl (meth)acrylates can be structurally represented by the following formula:

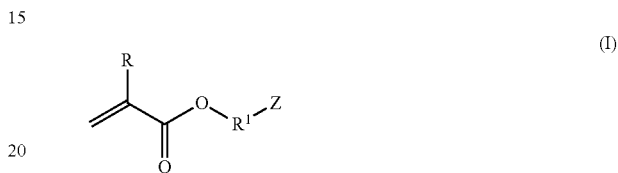

(I)

wherein R is hydrogen or methyl, $R^1$ is an divalent alkylene moiety containing 1 to 5 carbon atoms, and Z is —$NH_2$ or —OH, wherein the alkylene moiety optionally can be substituted by one or more methyl groups. Representative monomers include 2-aminoethyl(meth)acrylate, 2-hydroxyethyl(meth)acrylate, 3-hydroxypropyl(meth)acrylate, 4-hydroxybutyl(meth)acrylate, and mixtures thereof.

The amino group containing vinyl monomers include (meth)acrylamide, diacetone acrylamide and monomers that are structurally represented by the following formulas:

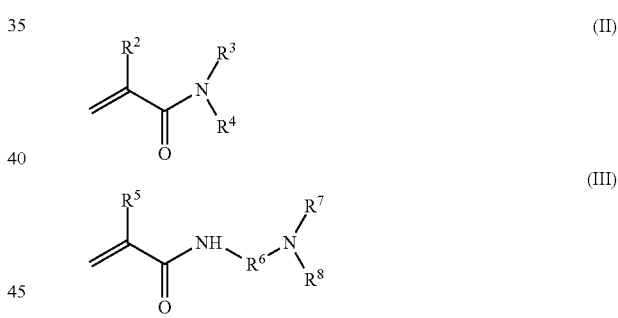

Formula (II) represents N—($C_1$-$C_5$)alkyl(meth)acrylamide or N,N-di($C_1$-$C_5$)alkyl(meth)acrylamide wherein $R^2$ is hydrogen or methyl, $R^3$ independently is selected from hydrogen, $C_1$ to $C_5$ alkyl and $C_1$ to $C_5$ hydroxyalkyl, and $R^4$ independently is selected from is $C_1$ to $C_5$ alkyl or $C_1$ to $C_5$ hydroxyalkyl.

Formula (III) represents N—($C_1$-$C_5$)alkylamino($C_1$-$C_5$) alkyl(meth)acrylamide or N,N-di($C_1$-$C_5$)alkylamino($C_1$-$C_5$) alkyl(meth)acrylamide wherein $R^5$ is hydrogen or methyl, $R^6$ is $C_1$ to $C_5$ alkylene, $R^7$ independently is selected from hydrogen or $C_1$ to $C_5$ alkyl, and $R^8$ independently is selected from $C_1$ to $C_5$ alkyl.

Representative N-alkyl(meth)acrylamides include but are not limited to N-methyl(meth)acrylamide, N-ethyl(meth)acrylamide, N-propyl(meth)acrylamide, N-isopropyl(meth)acrylamide, N-tert-butyl(meth)acrylamide, N-(2-hydroxyethyl)(meth)acrylamide, N-(3-hydroxypropyl)(meth)acrylamide, and mixtures thereof.

Representative N,N-dialkyl(meth)acrylamides include but are not limited to N,N-dimethyl(meth)acrylamide, N,N- diethyl(meth)acrylamide, N,N-(di-2-hydroxyethyl)(meth) acrylamide, N,N-(di-3-hydroxypropyl)(meth)acrylamide, N-methyl, N-ethyl(meth)acrylamide, and mixtures thereof.

Representative N,N-dialkylaminoalkyl(meth)acrylamides include but are not limited to N,N-dimethylaminoethyl (meth)acrylamide, N,N-diethylaminoethyl(meth)acrylamide, N,N-dimethylaminopropyl(meth)acrylamide, and mixtures thereof.

Hydrophobic Monomer

Hydrophobic monomers suitable for the preparation of the crosslinked, nonionic, amphiphilic polymer compositions of the invention are selected from but are not limited to one or more of alkyl esters of (meth)acrylic acid having an alkyl group containing 1 to 30 carbon atoms; vinyl ester of an aliphatic carboxylic acid containing an acyl moiety having 2 to 22 carbon atoms; vinyl ethers of alcohols containing 1 to 22 carbon atoms; vinyl aromatics containing 8 to 20 carbon atoms; vinyl halides; vinylidene halides; linear or branched alpha-monoolefins containing 2 to 8 carbon atoms; an alkoxylated associative monomer having a hydrophobic end group containing 8 to 30 carbon atoms, and mixtures thereof.

Semi-Hydrophobic Monomer

Optionally, at least one alkoxylated semi-hydrophobic monomer can be used in the preparation of the amphiphilic polymers of the invention. A semi-hydrophobic monomer is similar in structure to an associative monomer, but has a substantially non-hydrophobic end group selected from hydroxyl or a moiety containing 1 to 4 carbon atoms.

In one aspect of the invention, alkyl esters of (meth) acrylic acid having an alkyl group containing 1 to 22 carbon atoms can be represented by the following formula:

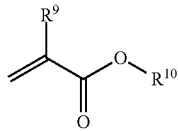

(IV)

wherein $R^9$ is hydrogen or methyl and $R^{10}$ is $C_1$ to $C_{22}$ alkyl group.

Representative monomers under formula (IV) include but are not limited to methyl (meth)acrylate, ethyl (meth)acrylate, butyl (meth)acrylate, sec-butyl (meth)acrylate, isobutyl (meth)acrylate, hexyl (meth)acrylate), heptyl (meth) acrylate, octyl (meth)acrylate, 2-ethylhexyl (meth)acrylate, decyl (meth)acrylate, isodecyl (meth)acrylate, lauryl (meth) acrylate, tetradecyl (meth)acrylate, hexadecyl (meth)acrylate, stearyl (meth)acrylate, behenyl (meth)acrylate, and mixtures thereof.

Vinyl esters of an aliphatic carboxylic acid containing an acyl moiety having 2 to 22 carbon atoms can be represented by the following formula:

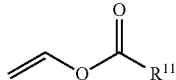

(V)

wherein $R^{11}$ is a $C_1$ to $C_{21}$ aliphatic group which can be an alkyl or alkenyl. Formula (V) contains an acyl moiety containing 2 to 22 carbon atoms. Representative monomers under formula (V) include but are not limited to vinyl acetate, vinyl propionate, vinyl butyrate, vinyl isobutyrate, vinyl valerate, vinyl hexanoate, vinyl 2-methylhexanoate, vinyl 2-ethylhexanoate, vinyl iso-octanoate, vinyl nonanoate, vinyl neodecanoate, vinyl decanoate, vinyl versatate, vinyl laurate, vinyl palmitate, vinyl stearate, and mixtures thereof.

In one aspect, the vinyl ethers of alcohols containing 1 to 22 carbon atoms can be represented by the following formula:

(VI)

wherein $R^{13}$ is a $C_1$ to $C_{22}$ alkyl. Representative monomers of formula (VI) include methyl vinyl ether, ethyl vinyl ether, butyl vinyl ether, isobutyl vinyl ether, 2-ethylhexyl vinyl ether, decyl vinyl ether, lauryl vinyl ether, stearyl vinyl ether, behenyl vinyl ether, and mixtures thereof.

Representative vinyl aromatic monomers include but are not limited to styrene, alpha-methylstyrene, 3-methyl styrene, 4-methyl styrene, 4-propyl styrene, 4-tert-butyl styrene, 4-n-butyl styrene, 4-n-decyl styrene, vinyl naphthalene, and mixtures thereof.

Representative vinyl and vinylidene halides include but are not limited to vinyl chloride and vinylidene chloride, and mixtures thereof.

Representative alpha-olefins include but are not limited to ethylene, propylene, 1-butene, iso-butylene, 1-hexene, and mixtures thereof.

The alkoxylated associative monomer of the invention has an ethylenically unsaturated end group portion (i) for addition polymerization with the other monomers of the invention; a polyoxyalkylene mid-section portion (ii) for imparting selective hydrophilic and/or hydrophobic properties to the product polymer, and a hydrophobic end group portion (iii) for providing selective hydrophobic properties to the polymer.

The portion (i) supplying the ethylenically unsaturated end group can be a residue derived from an α,β-ethylenically unsaturated monocarboxylic acid. Alternatively, portion (i) of the associative monomer can be a residue derived from an allyl ether or vinyl ether; a nonionic vinyl-substituted urethane monomer, such as disclosed in U.S. Reissue Pat. No. 33,156 or U.S. Pat. No. 5,294,692; or a vinyl-substituted urea reaction product, such as disclosed in U.S. Pat. No. 5,011,978; the relevant disclosures of each are incorporated herein by reference.

The mid-section portion (ii) is a polyoxyalkylene segment of about 2 to about 150 in one aspect, from about 10 to about 120 in another aspect, and from about 15 to about 60 in a further aspect, of repeating $C_2$-$C_4$ alkylene oxide units. The mid-section portion (ii) includes polyoxyethylene, polyoxypropylene, and polyoxybutylene segments, and combinations thereof comprising from about 2 to about 150 in one aspect, from about 5 to about 120 in another aspect, from about 10 to about 60 in a further aspect, and from about 15 to about 30 in a still further aspect, of ethylene, propylene and/or butylene oxide units, arranged in random or block sequences of ethylene oxide, propylene oxide and/or butylene oxide units.

The hydrophobic end group portion (iii) of the associative monomer is a hydrocarbon moiety belonging to one of the following hydrocarbon classes: a $C_8$-$C_{30}$ linear alkyl, a $C_8$-$C_{30}$ branched alkyl, a $C_2$-$C_{30}$ alkyl-substituted phenyl, aryl-substituted $C_2$-$C_{30}$ alkyl groups, a $C_7$-$C_{30}$ saturated or unsaturated carbocyclic alkyl group. The saturated or unsaturated carbocyclic moiety can be a $C_1$-$C_5$ alkyl substituted or unsubstituted monocyclic or bicyclic moiety. In one aspect, the bicyclic moiety is selected from bicycloheptyl or bicycloheptenyl. In another aspect, the bicycloheptenyl moiety is disubstituted with the alkyl substituent(s). In a further aspect, the bicycloheptenyl moiety is disubstituted with methyl on the same carbon atom.

Non-limiting examples of suitable hydrophobic end group portions (iii) of the associative monomers are linear or branched alkyl groups having about 8 to about 30 carbon atoms, such as capryl ($C_8$), iso-octyl (branched $C_8$), decyl ($C_{10}$), lauryl ($C_{12}$), myristyl ($C_{14}$), cetyl ($C_{15}$), cetearyl ($C_{16}$-$C_{18}$), stearyl ($C_{18}$), isostearyl (branched $C_{18}$), arachidyl ($C_{20}$), behenyl ($C_{22}$), lignoceryl ($C_{24}$), cerotyl ($C_{26}$), montanyl ($C_{28}$), melissyl ($C_{30}$), and the like.

Examples of linear and branched alkyl groups having about 8 to about 30 carbon atoms that are derived from a natural source include, without being limited thereto, alkyl groups derived from hydrogenated peanut oil, soybean oil and canola oil (all predominately $C_{18}$), hydrogenated tallow oil ($C_{16}$-$C_{18}$), and the like; and hydrogenated $C_{10}$-$C_{30}$ terpenols, such as hydrogenated geraniol (branched $C_{10}$), hydrogenated farnesol (branched $C_{15}$), hydrogenated phytol (branched $C_{20}$), and the like.

Non-limiting examples of suitable $C_2$-$C_{30}$ alkyl-substituted phenyl groups include octylphenyl, nonylphenyl, decylphenyl, dodecylphenyl, hexadecylphenyl, octadecylphenyl, isooctylphenyl, sec-butylphenyl, and the like.

Exemplary aryl-substituted $C_2$-$C_{40}$ alkyl groups include, without limitation, styryl (e.g., 2-phenylethyl), distyryl (e.g., 2,4-diphenylbutyl), tristyryl (e.g., 2,4,6-triphenylhexyl), 4-phenylbutyl, 2-methyl-2-phenylethyl, tristyrylphenolyl, and the like.

Suitable $C_7$-$C_{30}$ carbocyclic groups include, without limitation, groups derived from sterols from animal sources, such as cholesterol, lanosterol, 7-dehydrocholesterol, and the like; from vegetable sources, such as phytosterol, stigmasterol, campesterol, and the like; and from yeast sources, such as ergosterol, mycosterol, and the like. Other carbocyclic alkyl hydrophobic end groups useful in the present invention include, without limitation, cyclooctyl, cyclododecyl, adamantyl, decahydronaphthyl, and groups derived from natural carbocyclic materials, such as pinene, hydrogenated retinol, camphor, isobornyl alcohol, norbornyl alcohol, nopol and the like.

Useful alkoxylated associative monomers can be prepared by any method known in the art. See, for example, U.S. Pat. No. 4,421,902 to Chang et al.; U.S. Pat. No. 4,384,096 to Sonnabend; U.S. Pat. No. 4,514,552 to Shay et al.; U.S. Pat. No. 4,600,761 to Ruffner et al.; U.S. Pat. No. 4,616,074 to Ruffner; U.S. Pat. No. 5,294,692 to Barron et al.; U.S. Pat. No. 5,292,843 to Jenkins et al.; U.S. Pat. No. 5,770,760 to Robinson; U.S. Pat. No. 5,412,142 to Wilkerson, III et al.; and U.S. Pat. No. 7,772,421, to Yang et al., the pertinent disclosures of which are incorporated herein by reference.

In one aspect, exemplary alkoxylated associative monomers include those represented by formulas (VII) and (VIIA) as follows:

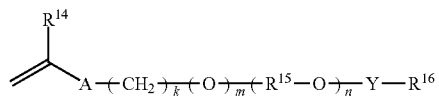

VII

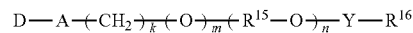

VIIA wherein $R^{14}$ is hydrogen or methyl; A is —$CH_2C(O)O$—, —$C(O)O$—, —$O$—, —$CH_2O$—, —$NHC(O)NH$—, —$C(O)NH$—, —Ar—$(CE_2)_z$-$NHC(O)O$—, —Ar—$(CE_2)_z$-$NHC(O)NH$—, or —$CH_2CH_2NHC(O)$—; Ar is a divalent arylene (e.g., phenylene); E is H or methyl; z is 0 or 1; k is an integer ranging from about 0 to about 30, and m is 0 or 1, with the proviso that when k is 0, m is 0, and when k is in the range of 1 to about 30, m is 1; D represents a vinyl or an allyl moiety; ($R^{15}$—$O$)$_n$ is a polyoxyalkylene moiety, which can be a homopolymer, a random copolymer, or a block copolymer of $C_2$-$C_4$ oxyalkylene units, $R^{15}$ is a divalent alkylene moiety selected from $C_2H_4$, $C_3H_6$, or $C_4H_8$, and combinations thereof; and n is an integer in the range of about 2 to about 150 in one aspect, from about 10 to about 120 in another aspect, and from about 15 to about 60 in a further aspect; Y is —$R^{15}O$—, —$R^{15}NH$—, —$O(O)$—, —$C(O)NH$—, —$R^{15}NHC(O)NH$—, —$C(O)NHC(O)$—, or a divalent alkylene radical containing 1 to 5 carbon atoms, e.g., methylene, ethylene, propylene, butylene, pentylene; $R^{16}$ is a substituted or unsubstituted alkyl selected from a $C_8$-$C_{30}$ linear alkyl, a $C_8$-$C_{30}$ branched alkyl, a $C_7$-$C_{30}$ carbocyclic, a $C_2$-$C_{30}$ alkyl-substituted phenyl, an araalkyl substituted phenyl, and an aryl-substituted $C_2$-$C_{30}$ alkyl; wherein the $R^{16}$ alkyl group, aryl group, phenyl group, or carbocyclic group optionally comprises one or more substituents selected from the group consisting of a methyl group, a hydroxyl group, an alkoxyl group, benzyl group phenylethyl group, and a halogen group. In one aspect, Y is ethylene and $R^{16}$ is

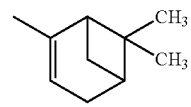

In one aspect, the hydrophobically modified alkoxylated associative monomer is an alkoxylated (meth)acrylate having a hydrophobic group containing 8 to 30 carbon atoms represented by the following Formula VB as follows:

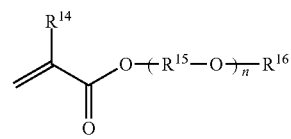

VIIB wherein $R^{14}$ is hydrogen or methyl; $R^{15}$ is a divalent alkylene moiety independently selected from $C_2H_4$, $C_3H_6$, and $C_4H_8$, and n represents an integer ranging from about 2 to about 150 in one aspect, from about 5 to about 120 in another aspect, from about 10 to about 60 in a further aspect, and from about 15 to about 30 in a still further aspect, ($R^{15}$—$O$) can be arranged in a random or a block configuration; $R^{16}$ is a substituted or unsubstituted alkyl selected from a $C_8$-$C_{30}$ linear alkyl, a $C_8$-$C_{30}$ branched alkyl, an alkyl substituted and unsubstituted $C_7$-$C_{30}$ carbocyclic alkyl, a $C_2$-$C_{30}$ alkyl-substituted phenyl, and an aryl-substituted $C_2$-$C_{30}$ alkyl.

Representative monomers under Formula V include lauryl polyethoxylated (meth)acrylate (LEM), cetyl polyethoxylated (meth)acrylate (OEM), cetearyl polyethoxylated (meth)acrylate (CSEM), stearyl polyethoxylated (meth)acrylate, arachidyl polyethoxylated (meth)acrylate, behenyl polyethoxylated (meth)acrylate (BEM), cerotyl polyethoxylated (meth)acrylate, montanyl polyethoxylated (meth)acrylate, melissyl polyethoxylated (meth)acrylate, phenyl polyethoxylated (meth)acrylate, nonylphenyl polyethoxylated (meth)acrylate, ω-tristyrylphenyl polyoxyethylene (meth)acrylate, where the polyethoxylated portion of the monomer contains about 2 to about 150 ethylene oxide units in one aspect, from about 5 to about 120 in another aspect, from about 10 to about 60 in a further aspect, and from about 15 to about 30 in a still further aspect; octyloxy polyethyleneglycol (8) polypropyleneglycol (6) (meth)acrylate, phenoxy polyethylene glycol (6) polypropylene glycol (6) (meth)acrylate, and nonylphenoxy polyethylene glycol polypropylene glycol (meth)acrylate.

The alkoxylated semi-hydrophobic monomers of the invention are structurally similar to the associative monomer described above, but have a substantially non-hydrophobic end group portion. The alkoxylated semi-hydrophobic monomer has an ethylenically unsaturated end group portion (i) for addition polymerization with the other monomers of the invention; a polyoxyalkylene mid-section portion (ii) for imparting selective hydrophilic and/or hydrophobic properties to the product polymer and a semi-hydrophobic end group portion (iii). The unsaturated end group portion (i) supplying the vinyl or other ethylenically unsaturated end group for addition polymerization is preferably derived from an α,β-ethylenically unsaturated mono carboxylic acid. Alternatively, the end group portion (i) can be derived from an allyl ether residue, a vinyl ether residue or a residue of a nonionic urethane monomer.

The polyoxyalkylene mid-section (ii) specifically comprises a polyoxyalkylene segment, which is substantially similar to the polyoxyalkylene portion of the associative monomers described above. In one aspect, the polyoxyalkylene portions (ii) include polyoxyethylene, polyoxypropylene, and/or polyoxybutylene units comprising from about 2 to about 150 in one aspect, from about 5 to about 120 in another aspect, from about 10 to about 60, and from about 15 to about 30 in a still further aspect, of ethylene oxide, propylene oxide, and/or butylene oxide units, arranged in random or blocky sequences.

In one aspect, the alkoxylated semi-hydrophobic monomer can be represented by the following formulas:

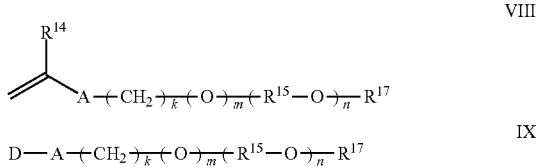

wherein $R^{14}$ is hydrogen or methyl; A is —CH$_2$C(O)O—, —C(O)O—, —O—, —CH$_2$O—, —NHC(O)NH—, —C(O)NH—, —Ar—(CE$_2$)$_z$-NHC(O)O—, —Ar—(CE$_2$)$_z$-NHC(O)NH—, or —CH$_2$CH$_2$NHC(O)—; Ar is a divalent arylene (e.g., phenylene); E is H or methyl; z is 0 or 1; k is an integer ranging from about 0 to about 30, and m is 0 or 1, with the proviso that when k is 0, m is 0, and when k is in the range of 1 to about 30, m is 1; $(R^{15}$—O$)_n$ is a polyoxyalkylene moiety, which can be a homopolymer, a random copolymer, or a block copolymer of $C_2$-$C_4$ oxyalkylene units, $R^{15}$ is a divalent alkylene moiety selected from $C_2H_4$, $C_3H_6$, or $C_4H_8$, and combinations thereof; and n is an integer in the range of about 2 to about 150 in one aspect, from about 5 to about 120 in another aspect, from about 10 to about 60 in still another aspect, and from about 15 to about 30 in a further aspect; $R^{17}$ is selected from hydrogen and a linear or branched $C_1$-$C_4$ alkyl group (e.g., methyl, ethyl, propyl, iso-propyl, butyl, iso-butyl, and tert-butyl); and D represents a vinyl or an allyl moiety.

In one aspect, the alkoxylated semi-hydrophobic monomer under formula VIII can be represented by the following formulas:

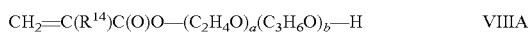

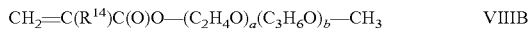

wherein $R^{14}$ is hydrogen or methyl, and "a" is an integer ranging from 0 or 2 to about 120 in one aspect, from about 5 to about 45 in another aspect, and from about 10 to about 0.25 in a further aspect, and "b" is an integer ranging from about 0 or 2 to about 120 in one aspect, from about 5 to about 45 in another aspect, and from about 10 to about 25 in a further aspect, subject to the proviso that "a" and "b" cannot be 0 at the same time.

Examples of alkoxylated semi-hydrophobic monomers under formula VIIIA include polyethyleneglycol methacrylate available under the product names Blemmer® PE-90 ($R^{14}$=methyl, a=2, b=0), PE-200 ($R^{14}$=methyl, a=4.5, b=0), and PE-350 ($R^{14}$=methyl a=8, b=0,); polypropylene glycol methacrylate available under the product names Blemmer® PP-1000 ($R^{14}$=methyl, b=4-6, a=0), PP-500 ($R^{14}$=methyl, a=0, b=9), PP-800 ($R^{14}$=methyl, a=0, b=13); polyethyleneglycol polypropylene glycol methacrylate available under the product names Blemmer® 50PEP-300 ($R^{14}$=methyl, a=3.5, b=2.5), 70PEP-350B ($R^{14}$=methyl, a=5, b=2); polyethyleneglycol acrylate available under the product names Blemmer® AE-90 ($R^{14}$=hydrogen, a=2, b=0), AE-200 ($R^{14}$=hydrogen, a=2, b=4.5), AE-400 ($R^{14}$=hydrogen, a=10, b=0); polypropyleneglycol acrylate available under the product names Blemmer® AP-150 ($R^{14}$=hydrogen, a=0, b=3), AP-400 ($R^{14}$=hydrogen, a=0, b=6), AP-550 ($R^{14}$=hydrogen, a=0, b=9). Blemmer® is a trademark of NOF Corporation, Tokyo, Japan.

Examples of alkoxylated semi-hydrophobic monomers under formula VIIIB include methoxypolyethyleneglycol methacrylate available under the product names Visiomer® MPEG 750 MAW ($R^{14}$=methyl, a=17, b=0), MPEG 1005 MAW ($R^{14}$=methyl, a=22, b=0), MPEG 2005 MAW ($R^{14}$=methyl, a=45, b=0), and MPEG 5005 MA W ($R^{14}$=methyl, a=113, b=0) from Evonik Röhm GmbH, Darmstadt, Germany); Bisomer® MPEG 350 MA ($R^{14}$=methyl, a=8, b=0), and MPEG 550 MA ($R^{14}$=methyl, a=12, b=0) from GEO Specialty Chemicals, Ambler Pa.; Blemmer® PME-100 ($R^{14}$=methyl, a=2, b=0), PME-200 ($R^{14}$=methyl, a=4, b=0), PME-400 ($R^{14}$=methyl, a=9, b=0), PME-1000 ($R^{14}$=methyl, a=23, b=0), PME-4000 ($R^{14}$=methyl, a=90, b=0).

In one aspect, the alkoxylated semi-hydrophobic monomer set forth in formula IX can be represented by the following formulas:

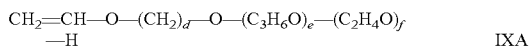

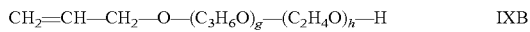

wherein d is an integer of 2, 3, or 4; e is an integer in the range of from about 1 to about 10 in one aspect, from about 2 to about 8 in another aspect, and from about 3 to about 7 in a further aspect; f is an integer in the range of from about 5 to about 50 in one aspect, from about 8 to about 40 in another aspect, and from about 10 to about 30 in a further aspect; g is an integer in the range of from 1 to about 10 in one aspect, from about 2 to about 8 in another aspect, and from about 3 to about 7 in a further aspect; and h is an integer in the range of from about 5 to about 50 in one aspect, and from about 8 to about 40 in another aspect; e, f, g, and h can be 0 subject to the proviso that e and f cannot be 0 at the same time, and g and h cannot be 0 at the same time.

Monomers under formulas IXA and IXB are commercially available under the trade names Emulsogen® R109, R208, R307, RAL109, RAL208, and RAL307 sold by Clariant Corporation; BX-AA-E5P5 sold by Bimax, Inc.; and combinations thereof. EMULSOGEN7 R109 is a randomly ethoxylated/propoxylated 1,4-butanediol vinyl ether having the empirical formula $CH_2=CH-O(CH_2)_4O(C_3H_6O)_4(C_2H_4O)_{10}H$; Emulsogen® R208 is a randomly ethoxylated/propoxylated 1,4-butanediol vinyl ether having the empirical formula $CH_2=CH-O(CH_2)_4O(C_3H_6O)_4(C_2H_4O)_{20}H$; Emulsogen® R307 is a randomly ethoxylated/propoxylated 1,4-butanediol vinyl ether having the empirical formula $CH_2=CH-O(CH_2)_4O(C_3H_6O)_4(C_2H_4O)_{30}H$; Emulsogen® RAL109 is a randomly ethoxylated/propoxylated allyl ether having the empirical formula $CH_2=CHCH_2O(C_3H_6O)_4(C_2H_4O)_{10}H$; Emulsogen® RAL208 is a randomly ethoxylated/propoxylated allyl ether having the empirical formula $CH_2=CHCH_2O(C_3H_6O)_4(C_2H_4O)_{20}H$; Emulsogen® RAL307 is a randomly ethoxylated/propoxylated allyl ether having the empirical formula $CH_2=CHCH_2O(C_3H_6O)_4(C_2H_4O)_{30}H$; and BX-AA-E5P5 is a randomly ethoxylated/propoxylated allyl ether having the empirical formula $CH_2=CHCH_2O(C_3H_6O)_5(C_2H_4O)_5H$.

Referring to the alkoxylated associative and the alkoxylated semi-hydrophobic monomers of the invention, the polyoxyalkylene mid-section portion contained in these monomers can be utilized to tailor the hydrophilicity and/or hydrophobicity of the polymers in which they are included. For example, mid-section portions rich in ethylene oxide moieties are more hydrophilic while mid-section portions rich in propylene oxide moieties are more hydrophobic. By adjusting the relative amounts of ethylene oxide to propylene oxide moieties present in these monomers the hydrophilic and hydrophobic properties of the polymers in which these monomers are included can be tailored as desired.

The amount of alkoxylated associative and/or semi-hydrophobic monomer utilized in the preparation of the polymers of the present invention can vary widely and depends, among other things, on the final rheological and aesthetic properties desired in the polymer. When utilized, the monomer reaction mixture contains one or more monomers selected from the alkoxylated associative and/or semi-hydrophobic monomers disclosed above in amounts ranging from about 0.5 to about 10 wt. % in one aspect, and from about 1, 2 or 3 to about 5 wt. % in a further aspect, based on the weight of the total monomers.

Ionizable Monomer

In one aspect, of the invention, the nonionic, amphiphilic polymer compositions of the invention can be polymerized from a monomer composition including 0 to 5 wt. % of an ionizable and/or ionized monomer, based on the weight of the total monomers, so long as the foaming properties and/or the yield stress value of the surfactant compositions in which the polymers of the invention are included are not deleteriously affected.

In another aspect, the amphiphilic polymer compositions of the invention can be polymerized from a monomer composition comprising less than 3 wt. % in one aspect, less than 1 wt. % in a further aspect, less than 0.5 wt. % in a still further aspect, less than 0.1 wt. % in an additional aspect, and less than 0.05 wt. % in a further aspect, of an ionizable and/or an ionized moiety, based on the weight of the total monomers.

Ionizable monomers include monomers having a base neutralizable moiety and monomers having an acid neutralizable moiety. Base neutralizable monomers include olefinically unsaturated monocarboxylic and dicarboxylic acids and their salts containing 3 to 5 carbon atoms and anhydrides thereof. Examples include (meth)acrylic acid, itaconic acid, maleic acid, maleic anhydride, and combinations thereof. Other acidic monomers include styrenesulfonic acid, acrylamidomethylpropanesulfonic acid (AMPS® monomer), vinylsulfonic acid, vinylphosphonic acid, allylsulfonic acid, methallylsulfonic acid; and salts thereof.

Acid neutralizable monomers include olefinically unsaturated monomers which contain a basic nitrogen atom capable of forming a salt or a quaternized moiety upon the addition of an acid. For example, these monomers include vinylpyridine, vinylpiperidine, vinylimidazole, vinylmethylimidazole, dimethylaminomethyl (meth)acrylate, dimethylaminoethyl (meth)acrylate, diethylaminomethyl (meth)acrylate and methacrylate, dimethylaminoneopentyl (meth)acrylate, dimethylaminopropyl (meth)acrylate, and diethylaminoethyl (meth)acrylate.

Crosslinking Monomer

In one embodiment, the crosslinked, nonionic, amphiphilic polymers useful in the practice of the invention are polymerized from a monomer composition comprising a first monomer comprising at least one nonionic, hydrophilic unsaturated monomer, at least one nonionic, unsaturated hydrophobic monomer, and mixtures thereof, and a third monomer comprising at least one polyunsaturated crosslinking monomer. The crosslinking monomer(s) is utilized to polymerize covalent crosslinks into the polymer backbone. In one aspect, the crosslinking monomer is a polyunsaturated compound containing at least 2 unsaturated moieties. In another aspect, the crosslinking monomer contains at least 3 unsaturated moieties. Exemplary polyunsaturated compounds include di(meth)acrylate compounds such as ethylene glycol di(meth)acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth)acrylate, neopentyl glycol di(meth)acrylate, 1,9-nonanediol di(meth)acrylate, 2,2'-bis(4-(acryloxy-propyloxyphenyl)propane, and 2,2'-bis(4-(acryloxydiethoxy-phenyl)propane; tri(meth)acrylate compounds such as, trimethylolpropane tri(meth)acrylate, trimethylolethane tri(meth)acrylate, and tetramethylolmethane tri(meth)acrylate; tetra(meth)acrylate compounds such as ditrimethylolpropane tetra(meth)acrylate, tetramethylolmethane tetra(meth)acrylate, and pentaerythritol tetra(meth)acrylate; hexa(meth)acrylate compounds such as dipentaerythritol hexa(meth)acrylate; allyl compounds such as allyl (meth)acrylate, diallylphthalate, diallyl itaconate, diallyl fumarate, and diallyl maleate; polyallyl ethers of sucrose having from 2 to 8 allyl groups per molecule, polyallyl ethers of pentaerythritol such as pentaerythritol diallyl ether, pentaerythritol triallyl ether, and pentaerythritol tetraallyl ether, and combinations thereof; polyallyl ethers of trimethylolpropane such as trimethylolpropane diallyl ether, trimethylolpropane triallyl ether, and combinations thereof. Other suitable polyunsaturated compounds include divinyl glycol, divinyl benzene, and methylenebisacrylamide.

In another aspect, suitable polyunsaturated monomers can be synthesized via an esterification reaction of a polyol made from ethylene oxide or propylene oxide or combinations thereof with unsaturated anhydride such as maleic anhydride, citraconic anhydride, itaconic anhydride, or an addition reaction with unsaturated isocyanate such as 3-isopropenyl-α-α-dimethylbenzene isocyanate.

Mixtures of two or more of the foregoing polyunsaturated compounds can also be utilized to crosslink the nonionic, amphiphilic polymers of the invention. In one aspect, the mixture of unsaturated crosslinking monomer contains an average of 2 unsaturated moieties. In another aspect, the mixture of crosslinking monomers contains an average of 2.5 unsaturated moieties. In still another aspect, the mixture of crosslinking monomers contains an average of about 3 unsaturated moieties. In a further aspect, the mixture of crosslinking monomers contains an average of about 3.5 unsaturated moieties.

In one embodiment of the invention, the amount of the crosslinking monomer ranges from 0 to about 1 wt. % in one aspect, from about 0.01 to about 0.75 wt. % in another aspect, from about 0.1 to about 0.5 in still another aspect, and from about 0.15 to about 0.3 wt. % in a still further aspect, all weight percentages are based on the dry weight of the nonionic, amphiphilic polymer of the invention.

In another embodiment of the invention, the crosslinking monomer component contains an average of about 3 unsaturated moieties and can be used in an amount ranging from about 0.01 to about 0.3 wt. % in one aspect, from about 0.02 to about 0.25 wt. % in another aspect, from about 0.05 to about 0.2 wt. % in a further aspect, and from about 0.075 to about 0.175 wt. % in a still further aspect, and from about 0.1 to about 0.15 wt. % in another aspect, based upon the dry weight of the, nonionic, amphiphilic polymer of the invention.

In one aspect, the crosslinking monomer is selected from trimethylolpropane tri(meth)acrylate, trimethylolethane tri(meth)acrylate, tetramethylolmethane tri(meth)acrylate, pentaerythritol triallylether and polyallyl ethers of sucrose having 3 allyl groups per molecule.

Amphiphilic Polymer Synthesis

The linear (non-crosslinked) and crosslinked, nonionic, amphiphilic polymers of the present invention can be made using conventional free-radical dispersion polymerization techniques. The polymerization process is carried out in the absence of oxygen under an inert atmosphere such as nitrogen. The polymerization can be carried out in a suitable organic solvent system such as a hydrocarbon solvent, organic solvent, or mixtures thereof. The polymerization reactions are initiated by any means which results in the generation of a suitable free-radical. Thermally derived radicals, in which the radical species is generated from thermal, homolytic dissociation of peroxides, hydroperoxides, persulfates, percarbonates, peroxyesters, hydrogen peroxide and azo compounds can be utilized. The initiators can be water soluble or water insoluble depending on the solvent system employed for the polymerization reaction.

The initiator compounds can be utilized in an amount of up to 30 wt. % in one aspect, 0.01 to 10 wt. % in another aspect, and 0.2 to 3 wt. % in a further aspect, based on the total weight of the dry polymer.

Exemplary free radical water soluble initiators include, but are not limited to, inorganic persulfate compounds, such as ammonium persulfate, potassium persulfate, and sodium persulfate; peroxides such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid, and water soluble azo compounds, such as 2,2'-azobis(tert-alkyl) compounds having a water solubilizing substituent on the alkyl group. Exemplary free radical oil soluble compounds include, but are not limited to 2,2'-azobisisobutyronitrile, and the like. The peroxides and peracids can optionally be activated with reducing agents, such as sodium bisulfite, sodium formaldehyde, or ascorbic acid, transition metals, hydrazine, and the like.

In one aspect, azo polymerization catalysts include the Vazo® free-radical polymerization initiators, available from DuPont, such as Vazo® 44 (2,2'-azobis(2-(4,5-dihydroimidazolyl)propane), Vazo® 56 (2,2'-azobis(2-methylpropionamidine) dihydrochloride), Vazo® 67 (2,2'-azobis(2-methylbutyronitrile)), and Vazo® 68 (4,4'-azobis(4-cyanovaleric acid)).

Optionally, the use of known redox initiator systems as polymerization initiators can be employed. Such redox initiator systems include an oxidant (intiator) and a reductant. Suitable oxidants include, for example, hydrogen peroxide, sodium peroxide, potassium peroxide, t-butyl hydroperoxide, t-amyl hydroperoxide, cumene hydroperoxide, sodium perborate, perphosphoric acid and salts thereof, potassium permanganate, and ammonium or alkali metal salts of peroxydisulfuric acid, typically at a level of 0.01% to 3.0% by weight, based on dry polymer weight, are used. Suitable reductants include, for example, alkali metal and ammonium salts of sulfur-containing acids, such as sodium sulfite, bisulfite, thiosulfate, hydrosulfite, sulfide, hydrosulfide or dithionite, formadinesulfinic acid, hydroxymethanesulfonic acid, acetone bisulfite, amines such as ethanolamine, glycolic acid, glyoxylic acid hydrate, ascorbic acid, isoascorbic acid, lactic acid, glyceric acid, malic acid, 2-hydroxy-2-sulfinatoacetic acid, tartaric acid and salts of the preceding acids typically at a level of 0.01% to 3.0% by weight, based on dry polymer weight, is used. In one aspect, combinations of peroxodisulfates with alkali metal or ammonium bisulfites can be used, for example, ammonium peroxodisulfate and ammonium bisulfite. In another aspect, combinations of hydrogen peroxide containing compounds (t-butyl hydroperoxide) as the oxidant with ascorbic or erythorbic acid as the reductant can be utilized. The ratio of peroxide-containing compound to reductant is within the range from 30:1 to 0.05:1.

Examples of suitable hydrocarbon solvents or diluents that can be utilized in the polymerization medium are aromatic solvents such as toluene, o-xylene, p-xylene, cumene, chlorobenzene, and ethylbenzene, aliphatic hydrocarbons, such as pentane, hexane, heptane, octane, nonane, decane, and the like, halogenated hydrocarbons, such as methylene chloride, alicyclic hydrocarbons, such as cyclopentane, methyl cyclopentane, cyclohexane, cycloheptane, cyclooctane, cyclononane, cyclodecane, and the like, and mixtures thereof. Suitable organic solvents include acetone, cyclohexanone, tetrahydrofuran, dioxane, glycols and glycol derivatives, polyalkylene glycols and derivatives thereof, diethyl ether, tert-butyl methyl ether, methyl acetate, ethyl acetate, propyl acetate, isopropyl acetate, butyl acetate, butyl propionate, and mixtures thereof. Mixtures of hydrocarbon solvents and organic solvents are also useful.

In the dispersion polymerization process, it can be advantageous to stabilize the monomer/polymer droplets or particles by means of surface active auxiliaries. Typically, these are emulsifiers, protective colloids or dispersion stabilizing polymers. The surface active auxiliaries used can be anionic, nonionic, cationic or amphoteric. Examples of anionic emulsifiers are alkylbenzenesulfonic acids, sulfonated fatty acids, sulfosuccinates, fatty alcohol sulfates, alkylphenol sulfates and fatty alcohol ether sulfates. Examples of usable nonionic emulsifiers are alkylphenol ethoxylates, primary alcohol ethoxylates, fatty acid ethoxylates, alkanolamide ethoxylates, fatty amine ethoxylates, EO/PO block copolymers and alkylpolyglucosides. Examples of cationic and amphoteric emulsifiers used are quaternized amine alkoxylates, alkylbetaines, alkylamidobetaines and sulfobetaines.

Examples of typical protective colloids are cellulose derivatives, polyethylene glycol, polypropylene glycol, copolymers of ethylene glycol and propylene glycol, polyvinyl acetate, poly(vinyl alcohol), partially hydrolyzed poly (vinyl alcohol), polyvinyl ether, starch and starch derivatives, dextran, polyvinylpyrrolidone, polyvinylpyridine, polyethyleneimine, polyvinylimidazole, polyvinylsuccinimide, polyvinyl-2-methylsuccinimide, polyvinyl-1,3-oxazolid-2-one, polyvinyl-2-methylimidazoline and maleic acid or anhydride copolymers. The emulsifiers or protective colloids are customarily used in concentrations from 0.05 to 20 wt. %, based on the weight of the total monomers.

Examples of typical protective colloids are cellulose derivatives, polyethylene glycol, polypropylene glycol, copolymers of ethylene glycol and propylene glycol, polyvinyl acetate, poly(vinyl alcohol), partially hydrolyzed poly (vinyl alcohol), polyvinyl ether, starch and starch derivatives, dextran, polyvinylpyrrolidone, polyvinylpyridine, polyethyleneimine, polyvinylimidazole, polyvinylsuccinimide, polyvinyl-2-methylsuccinimide, polyvinyl-1,3-oxazolid-2-one, polyvinyl-2-methylimidazoline and maleic acid or anhydride copolymers. The emulsifiers or protective colloids are customarily used in concentrations from 0.05 to 20 wt. %, based on the weight of the total monomers.

The polymerization can be carried out the presence of chain transfer agents. Suitable chain transfer agents include, but are not limited to, thio- and disulfide containing compounds, such as $C_1$-$C_{18}$ alkyl mercaptans, such as tert-butyl mercaptan, n-octyl mercaptan, n-dodecyl mercaptan, tert-dodecyl mercaptan hexadecyl mercaptan, octadecyl mercaptan; mercaptoalcohols, such as 2-mercaptoethanol, 2-mercaptopropanol; mercaptocarboxylic acids, such as mercaptoacetic acid and 3-mercaptopropionic acid; mercaptocarboxylic acid esters, such as butyl thioglycolate, isooctyl thioglycolate, dodecyl thioglycolate, isooctyl 3-mercaptopropionate, and butyl 3-mercaptopropionate; thioesters; $C_1$-$C_{18}$ alkyl disulfides; aryldisulfides; polyfunctional thiols such as trimethylolpropane-tris-(3-mercaptopropionate), pentaerythritol-tetra-(3-mercaptopropionate), pentaerythritol-tetra-(thioglycolate), pentaerythritol-tetra-(thiolactate), dipentaerythritol-hexa-(thioglycolate), and the like; phosphites and hypophosphites; $C_1$-$C_4$ aldehydes, such as formaldehyde, acetaldehyde, propionaldehyde; haloalkyl compounds, such as carbon tetrachloride, bromotrichloromethane, and the like; hydroxylammonium salts such as hydroxylammonium sulfate; formic acid; sodium bisulfite; isopropanol; and catalytic chain transfer agents such as, for example, cobalt complexes (e.g., cobalt (II) chelates).

The chain transfer agents are generally used in amounts ranging from 0.1 to 10 wt. %, based on the total weight of the monomers present in the polymerization medium.

In another aspect of the invention, the nonionic, amphiphilic polymer is obtained by free-radical mediated dispersion polymerization in a non-aqueous medium that is a solvent for the monomers but a substantially non-solvent for the resulting polymers. Non-aqueous dispersion polymerization is discussed in detail in the book *Dispersion Polymerization in Organic Media*, edited by K. E. G. Barrett and published by John Wiley & Sons, New York, 1975. In a typical procedure for preparing a dispersion polymer, an organic solvent containing the polymerizable monomers, any polymerization additives such as processing aids, chelants, pH buffers and a stabilizer polymer is charged to an oxygen purged, temperature controlled reactor equipped with a mixer, a thermocouple, a nitrogen purging tube, and a reflux condenser. The reaction medium is mixed vigorously, heated to the desired temperature, and then a free-radical initiator is added. The polymerization is usually conducted at reflux temperature to prevent oxygen from inhibiting the reaction. Reflux temperature typically falls in the range of from about 40° C. to about 200° C. in one aspect, and from about 60° C. to about 140° C. in another aspect, depending on the boiling point of the solvents comprising the non-aqueous medium in which the polymer is prepared. The reaction medium is continually purged with nitrogen while maintaining temperature and mixing for several hours. After this time, the mixture is cooled to room temperature, and any post-polymerization additives are charged to the reactor. Hydrocarbons are preferably used as the dispersion solvent. The reaction time required in such a polymerization will vary with the reaction temperature employed, initiator system, and initiator level. Generally, this reaction time will vary from about 20 minutes up to about 30 hours. Commonly, it will be preferred to utilize a reaction time from about 1 up to about 6 hours.

Typically, polymerization of the monomers used to prepare the polymers is initiated by free-radical initiators that are soluble in the non-aqueous medium. Examples include azo compound initiators such as 2,2'-azobis (2,4-dimethylpentane nitrile), 2,2'-azobis(2-methylbutanenitrile), and 2,2'-azobis(2-methylbutyronitrile). The initiators can be used in customary amounts, for example 0.05 to 7 wt. %, based on the amount of monomers to be polymerized.

In one aspect, the solvent is a hydrocarbon selected from aliphatic and cycloaliphatic solvents, as well as mixtures thereof. Exemplary hydrocarbon solvents include pentane, hexane, heptane, octane, nonane, decane, cyclopentane, methyl cyclopentane, cyclohexane, cycloheptane, cyclooctane, cyclononane, cyclodecane, and their mixtures.

In another aspect, the solvent is an organic solvent selected from acetone, cyclohexanone, tetrahydrofuran, dioxane, glycols and glycol derivatives, polyalkylene glycols and derivatives thereof, diethyl ether, tert-butyl methyl ether, methyl acetate, methyl acetate, ethyl acetate, propyl acetate, isopropyl acetate, butyl acetate, butyl propionate, ethanol, isopropanol, water, and mixtures thereof.

The amount of solvent utilized normally will be in excess of the monomers to be polymerized and the proportion can vary from at least 1 wt. % of the monomer components and 99 wt. % solvent, up to about 65 wt. % polymerizable monomer components and 35 wt. % solvent. In another aspect, a concentration of about 10 to 60 wt. % polymerizable monomer components can be employed, where the weight percent is based on the total amount of monomer and solvent charged to the reaction vessel.

When mixtures of organic solvents and hydrocarbon solvents are utilized, the organic solvents and the hydrocarbon solvents can be premixed or can be added separately to the reaction mixture and the polymerization reaction can be carried out thereafter. The relative weight ratio of the at least one organic solvent to at the least one hydrocarbon solvent can be in the range of from about 95/5 to about 1/99 in one aspect, from about 80/20 to about 5/95 in another aspect, and from about 2:1 to 1:2 in a further aspect.

In one aspect the ratio of hydrocarbon solvent to organic solvent is 70/30 wt./wt. In one aspect the hydrocarbon solvent is selected from cyclohexane and the organic solvent is selected from ethyl acetate.

The stabilizer, typically a block or graft copolymer, prevents settling of the desired solid polymer product produced during the reaction. The block copolymer dispersion stabilizer can be selected from a variety of polymers containing at least two blocks wherein at least one of said blocks ("A" block) is soluble in the dispersion medium and at least another of said blocks ("B" block) is insoluble in the dispersion medium, and the stabilizer acts to disperse polymer products which are formed in the stabilizer's presence. The insoluble "B" block provides an anchor segment for attachment to the obtained polymer product, thus reducing the solubility of the polymerized product in the dispersion medium. The soluble "A" block of the dispersion stabilizer provides a sheath around the otherwise insoluble polymer and maintains the polymeric product as numerous small discrete particles rather than an agglomerated or highly coalesced mass. Details of the mechanism of such steric stabilization are described in Napper, D. H., "Polymeric Stabilization of Colloidal Dispersions," Academic Press, New York, N.Y., 1983. Representative stabilizers useful in the dispersion polymerization process of the invention are disclosed in U.S. Pat. Nos. 4,375,533; 4,419,502; 4,526,937; 4,692,502; 5,288,814; 5,349,030; 5,373,044; 5,468,797; and 6,538,067, which are incorporated herein by reference.

In one aspect of the invention, the steric stabilizer is selected from poly(12-hydroxystearic acid) such as disclosed in U.S. Pat. No. 5,288,814. In another aspect of the invention, the steric stabilizer comprises the ester of the reaction product of a $C_{18}$-$C_{24}$ hydrocarbyl substituted succinic acid or the anhydride thereof with a polyol such as disclosed in U.S. Pat. No. 7,044,988. In another aspect, the steric stabilizer comprises the ester of the reaction product of a $C_{20}$ to $C_{24}$ alkyl substituted succinic anhydride and a polyol selected from glycerin and/or a polyglycerol containing 2 to 6 glycerin units. U.S. Pat. Nos. 5,288,814 and 7,044,988 are herein incorporated by reference.

In still another aspect, the steric stabilizer is a copolymer of N-vinyl pyrrolidone/stearyl methacrylate/butyl acrylate. In one aspect, the comonomers are incorporated into the stabilizer polymer in a weight ratio of 50/30/20, respectively. Mixtures of this steric stabilizer with esters and half esters of the reaction product of the $C_{12}$ to $C_{30}$ alkenyl substituted succinic anhydride and a polyol selected from $C_2$ to $C_4$ glycols are also contemplated.

The amount of steric stabilizer used in the polymerization process of this invention will cause variations in the size and specific surface area of the disperse polymer. In general, the amount of stabilizer utilized can range from 0.1 to 10 wt. % based on the dry polymer weight. Of course, smaller particles of disperse polymer require more stabilizer than large particles of disperse polymer.

In one feature, the nonionic, amphiphilic polymer suitable for use in the compositions of the invention is selected from a dispersion polymer that is prepared from a polymerizable monomer mixture comprising a combination of at least one vinyl lactam, at least one vinyl ester of an aliphatic carboxylic acid containing an acyl moiety having 2 to 22 carbon atoms, and an optional monomer selected from at least one crosslinking monomer, at least one $C_1$-$C_{30}$ alkyl ester of (meth)acrylic acid, at least one alkoxylated associative monomer, at least one alkoxylated semi-hydrophobic monomer, and mixtures thereof.

The amount of the at least one vinyl lactam monomer in the monomer mixture ranges from about 55 to about 95 wt. % in one aspect, from about 60 to about 90 wt. % in another aspect, from about 65 to about 85 wt. % in a further aspect, and from about 70 to about 80 wt. % in a still further aspect, all weight percentages are based on the total weight of the monomers in the monomer mixture. In one aspect, the at least one vinyl lactam monomer is selected from N-vinyl pyrrolidone.

The amount of the at least one vinyl ester of an aliphatic carboxylic acid containing an acyl moiety having 2 to 22 carbon atoms in the monomer mixture ranges from about 5 to about 45 wt. % in one aspect, from about 10 to about 40 wt. % in another aspect, from about 15 to about 35 wt. % in a further aspect, and from about 20 to 30 wt. % in a still further aspect, all weight percentages are based on the total weight of the monomers in the monomer mixture. In one aspect, the at least one vinyl ester of an aliphatic carboxylic acid containing an acyl moiety having 2 to 22 carbon atoms is selected from vinyl acetate.

The amount of the at least one crosslinking monomer present in the monomer mixture ranges from 0 to about 1 wt. % in one aspect, from about 0.01 to about 0.75 wt. % in another aspect, from about 0.1 to about 0.5 in still another aspect, and from about 0.15 to about 0.3 wt. % in a still further aspect, all weight percentages are based on the dry weight of the nonionic, amphiphilic polymer of the invention. In one aspect, the crosslinking monomer is selected from trimethylolpropane tri(meth)acrylate, trimethylolethane tri(meth)acrylate, tetramethylolmethane tri(meth)acrylate, pentaerythritol triallylether and polyallyl ethers of sucrose having 3 allyl groups per molecule.

The amount of the at least one $C_1$-$C_{30}$ alkyl ester of (meth)acrylic acid monomer ranges 0 to about 10 wt. % in one aspect, from about 0.1 to about 5 wt. % in another aspect, from about 0.5 to about 3 wt. % in a further aspect, and from about 0.75 to about 1 wt. % in a still further aspect, all weight percentages are based on the total weight of the monomers in the monomer mixture. In one feature of the invention a suitable monomer is selected from at least one $C_1$ to $C_{22}$ alkyl ester of (meth)acrylic acid. In another feature a suitable monomer is selected from a $C_{10}$ to $C_{22}$ alkyl ester of (meth)acrylic acid. Exemplary monomers include methyl (meth)acrylate, ethyl (meth)acrylate, butyl (meth)acrylate, sec-butyl (meth)acrylate, iso-butyl (meth)acrylate, hexyl (meth)acrylate), heptyl (meth)acrylate, octyl (meth)acrylate, 2-ethylhexyl (meth)acrylate, decyl (meth)acrylate, isodecyl (meth), lauryl (meth)acrylate, tetradecyl (meth)acrylate, hexadecyl (meth)acrylate, stearyl (meth)acrylate, behenyl (meth)acrylate, and mixtures thereof.

The amount of the at least one alkoxylated associative monomer ranges from about 0 to about 8 wt. % in one aspect, and from about 0.5, 1, 2 or 3 to about 5 wt. % in a further aspect, based on the weight of the total monomers in the monomer mixture. In one aspect, the at least one alkoxylated associative monomer is selected from lauryl polyethoxylated methacrylate (LEM), cetyl polyethoxylated methacrylate (OEM), cetearyl polyethoxylated methacrylate (CSEM), stearyl polyethoxylated (meth)acrylate, arachidyl polyethoxylated (meth)acrylate, behenyl polyethoxylated methacrylate (BEM), or mixtures thereof, wherein the amount of ethoxylation ranges from about 5 to 60 ethylene oxide units.

The amount of the at least one alkoxylated semi-hydrophobic monomer in the monomer mixture ranges from about 0 to about 10 wt. % in one aspect, and from about 0.5, 1, 2 or 3 to about 5 wt. % in a further aspect, based on the weight of the total monomers in the monomer mixture. In one aspect a suitable alkoxylated semi-hydrophobic monomer is selected from at least one monomer conforming to formulas VIIIA and VIIIB described above.

The weight percentages of the monomers set forth above and throughout the specification that are contained in the polymerizable monomer mixture are selected from the disclosed ranges such that the sum of the total amount of monomers in the monomer mixture is 100 wt. %.

The cleansing compositions of the invention comprise at least one anionic detersive surfactant, at least one nonionic amphiphilic polymer which improves foaming performance, water, and optional adjuvants and additives known in the personal care formulation art.

In one general aspect of the invention, the crosslinked, nonionic, amphiphilic polymer component of the cleansing composition is prepared by polymerizing a monomer mixture comprising:
  a) from about 55 to about 95 wt. % N-vinyl pyrrolidone;
  b) from about 5 to about 45 wt. % of vinyl acetate;
  c) from about 0 or 0.1, or 0.15, or 0.3, or 0.75 to about 1 wt. %, of at least one polyunsaturated crosslinking monomer containing at least two polymerizable ethylenically unsaturated moieties;
  d) from about 0 or 0.5, 1, 2 or 3 to about 5 wt. % of at least one $C_1$ to $C_{22}$ alkyl ester of (meth)acrylic acid;
  e) from about 0 or 0.5, 1, 2 or 3 to about 5 wt. % of at least one alkoxylated associative monomer;
  f) from about 0 or 0.5, 1, 2 or 3 to about 5 wt. % of at least one alkoxylated semi-hydrophobic monomer;
  g) from about 0 or 0.5, 1, 2 or 3 to about 5 wt. % of a vinyl ester of an aliphatic carboxylic acid containing an acyl moiety having 2 to 22 carbon atoms other than vinyl acetate; and combinations of monomers c) through g).

Detersive Compositions

The present crosslinked, nonionic, amphiphilic, polymer component of the cleansing composition is activated by the anionic surfactant to providing a stable yield stress cleansing composition with desirable rheological and aesthetic properties and the ability to suspend particulate and insoluble materials in an aqueous medium for indefinite periods of time independent of pH. Surprisingly, the polymer component of the cleansing composition enhances the foam properties of the composition. The nonionic, amphiphilic, polymers of the invention are useful in the pH range of from about 2 to about 14 in one aspect, from about 3 to 11 in another aspect, and from about 4 to about 9 in a further aspect. Unlike the pH responsive acrylic acid containing polymers that require neutralization with an acid or a base to impart a desired property to the composition in which it is included, the properties provided by the crosslinked, nonionic, amphiphilic polymers of the invention are substantially independent of pH. By substantially independent of pH is meant that the polymer component of the invention imparts an enhanced forming property and a desired rheological profile (e.g., a yield stress of at least 0.1 Pa in one aspect, at least at least 0.5 Pa in another aspect, at least 1 Pa in still another aspect, and at least 2 Pa in a further aspect) across a wide pH range (e.g., from about 2 to about 14) wherein the standard deviation in yield stress values across the pH range is less than 1 Pa in one aspect, less than 0.5 Pa in another aspect, and less than 0.25 Pa in a further aspect of the invention.

Suitable anionic detersive surfactant components for use in the cleansing compositions of the invention include those which are known for use in personal care or home care cleansing and detersive compositions.

In one exemplary aspect of the invention, the cleansing compositions comprise: i) at least one crosslinked, nonionic, amphiphilic, polymer of the invention; ii) at least one surfactant selected from at least one anionic surfactant, at least one amphoteric surfactant, at least one nonionic surfactant, and combinations thereof; and iii) water.

In another exemplary aspect of the invention, the cleansing compositions comprise: i) at least one crosslinked, nonionic, amphiphilic, polymer of the invention; ii) at least one anionic surfactant; and iii) water.

In another exemplary aspect of the invention, the cleansing compositions comprise: i) at least one crosslinked, nonionic, amphiphilic, polymer of the invention; ii) at least one anionic surfactant; iii) at least one amphoteric surfactant; and iv) water.

In another exemplary aspect of the invention, the cleansing compositions comprise: i) at least one crosslinked, nonionic, amphiphilic, polymer of the invention; ii) at least one anionic surfactant, iii) at least one nonionic surfactant; and iv) water.

In another exemplary aspect of the invention, the cleansing compositions comprise: i) at least one crosslinked, nonionic, amphiphilic, polymer of the invention; ii) at least one anionic surfactant, iii) at least one amphoteric surfactant; iv) at least one nonionic surfactant; and v) water.

In another exemplary aspect of the invention, the cleansing compositions comprise: i) at least one crosslinked, nonionic, amphiphilic, polymer of the invention; ii) at least one anionic ethoxylated surfactant; iii) an optional nonionic surfactant; and iv) water. In one aspect, the average degree of ethoxylation of the anionic ethoxylated surfactant can range from about 1 to about 3. In another aspect, the average degree of ethoxylation is about 2.

In another exemplary aspect of the invention, the cleansing compositions comprise: i) at least one crosslinked, nonionic, amphiphilic, polymer of the invention; ii) at least one anionic ethoxylated surfactant; iii) at least one amphoteric surfactant; iv) an optional nonionic surfactant; and v) water. In one aspect, the average degree of ethoxylation of the anionic ethoxylated surfactant can range from about 1 to about 3. In another aspect, the average degree of ethoxylation is about 2.

In another exemplary aspect of the invention, the cleansing compositions comprise: i) at least one crosslinked, nonionic, amphiphilic, polymer of the invention; ii) at least one anionic non-ethoxylated surfactant; iii) an optional anionic ethoxylated surfactant; iv) an optional nonionic surfactant; and v) water. In one aspect, the average degree of ethoxylation of the anionic ethoxylated surfactant can range from about 1 to about 3. In another aspect, the average degree of ethoxylation is about 2.

In another exemplary aspect of the invention, the cleansing compositions comprise: i) at least one crosslinked, nonionic, amphiphilic, polymer of the invention; ii) at least one anionic non-ethoxylated surfactant; iii) at least one anionic ethoxylated surfactant; iv) at least one amphoteric surfactant; v) an optional nonionic surfactant; and v) water. In one aspect, the average degree of ethoxylation in the anionic ethoxylated surfactant can range from about 1 to about 3. In another aspect, the average degree of ethoxylation is about 2.

In one aspect, the amount of nonionic, amphiphilic polymer that can be incorporated into the surfactant containing cleansing and detersive compositions of the invention ranges from about 0.5 to about 5 wt. % polymer solids (100% active polymer) based on the weight of the total composition. In another aspect, the amount of polymer utilized in the formulation ranges from about 0.75 wt. % to about 3.5 wt. %. In still another aspect, the amount of amphiphilic polymer employed in the cleansing composition ranges from about 1 to about 3 wt. %. In a further aspect, the amount of polymer employed in the cleansing composition ranges from about 1.5 wt. % to about 2.75 wt. %. In a still further aspect, the amount of polymer utilized in the cleansing composition ranges from about 2 to about 2.5 wt. %.

In one aspect, the at least one nonionic, amphiphilic polymer utilized in formulating the cleansing compositions of the invention is linear. In one aspect, the number average molecular weight ($M_n$) of the linear copolymeric mitigants of the present invention as measured by gel permeation chromatography (GPC) calibrated with a poly(methyl methacrylate) (PMMA) standard is 500,000 daltons or less. In another aspect, the molecular weight is 100,000 daltons or less. In still another aspect, the molecular weight ranges between about 5,000 and about 80,000 daltons, in a further aspect between about 10,000 and 50,000 daltons, and in a still further aspect between about 15,000 and 40,000 daltons.

In another aspect, the at least one nonionic, amphiphilic polymer utilized in formulating the mild cleansing compositions of the invention is crosslinked. The crosslinked nonionic, amphiphilic polymers of the invention are random copolymers and have weight average molecular weights ranging from above about 500,000 to at least about 4.5 billion Daltons or more in one aspect, and from about 600,000 to about a billion Daltons in another aspect, and from about 1,000,000 to about 3,000,000 Daltons in a further aspect, and from about 1,500,000 to about 2,000,000 Daltons in a still further aspect (see TDS-222, Oct. 15, 2007, Lubrizol Advanced Materials, Inc., which is herein incorporated by reference).

Detersive Surfactants

The surfactants utilized to formulate the cleansing and conditioning compositions of the invention are chosen from at least one detersive surfactant selected from at least one anionic surfactant, and an optional surfactant selected from amphoteric surfactants, nonionic surfactants, and mixtures thereof.

Non-limiting examples of anionic surfactants are disclosed in *McCutcheon's Detergents and Emulsifiers*, North American Edition, 1998, published by Allured Publishing Corporation; and McCutcheon's, *Functional Materials*, North American Edition (1992); both of which are incorporated by reference herein in their entirety. The anionic surfactant can be any of the anionic surfactants known or previously used in the art of aqueous surfactant compositions. Suitable anionic surfactants include but are not limited to alkyl sulfates, alkyl ether sulfates alkyl sulfonates, alkylaryl sulfonates, alkenyl and hydroxyalkyl alpha-olefin-sulfonates, and mixtures thereof, alkylamide sulfonates, alkarylpolyether sulphates, alkylamidoether sulphates, alkyl and alkenyl monoglyceryl ether sulfates, alkyl and alkenyl monoglyceride sulfates, alkyl and alkenyl monoglyceride sulfonates, alkyl and alkenyl succinates, alkyl and alkenyl sulfosuccinates, alkyl and alkenyl sulfosuccinamates, alkyl and alkenyl ether sulfosuccinates, alkyl and alkenyl amidosulfosuccinates; alkyl and alkenyl sulphoacetates, alkyl and alkenyl phosphates, alkyl and alkenyl ether phosphates, alkyl and alkenyl carboxylates, alkyl and alkenyl ether carboxylates, alkyl and alkenyl amidoethercarboxylates, N-alkylamino acids, N-acyl amino acids, alkyl peptides, N-acyl taurates, acyl isethionates, carboxylate salts wherein the acyl group is derived from fatty acids; and the alkali metal, alkaline earth metal, ammonium, amine, and triethanolamine salts thereof.

In one aspect, the cation moiety of the forgoing salts is selected from sodium, potassium, magnesium, ammonium, mono-, di- and triethanolamine salts, and mono-, di-, and tri-isopropylamine salts. The alkyl and acyl groups of the foregoing surfactants contain from about 6 to about 24 carbon atoms in one aspect, from 8 to 22 carbon atoms in another aspect, and from about 12 to 18 carbon atoms in a further aspect, and can be saturated or unsaturated. The aryl groups in the surfactants are selected from phenyl or benzyl. The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include but are not limited to the sodium, potassium, lithium, magnesium, ammonium, and triethanolamine lauryl sulfate, coco sulfate, tridecyl sulfate, myristyl sulfate, cetyl sulfate, cetearyl sulfate, stearyl sulfate, oleyl sulfate, and tallow sulfate; the sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, 3, 4 or 5 moles of ethylene oxide; disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcocinate, sodium dodecylbenzene sulfonate, sodium cocoyl sarcosinate, sodium cocoyl glutamate, potassium myristoyl glutamate, triethanolamine monolauryl phosphate, and fatty acid soaps, including the sodium, potassium, ammonium, and triethanolamine salts of a saturated and unsaturated fatty acids containing from about 8 to about 22 carbon atoms.

The term "amphoteric surfactant" as used herein, is also intended to encompass zwitterionic surfactants, which are well known to formulators skilled in the art as a subset of amphoteric surfactants. Non-limiting examples of amphoteric surfactants are disclosed *McCutcheon's Detergents and Emulsifiers*, North American Edition, supra, and McCutcheon's, *Functional Materials*, North American Edition, supra; both of which are incorporated by reference herein in their entirety. Suitable examples include but are not limited to amino acids (e.g., N-alkyl amino acids and N-acyl amino acids), betaines, sultaines, and alkyl amphocarboxylates.

Amino acid based surfactants suitable in the practice of the present invention include surfactants represented by the formula:

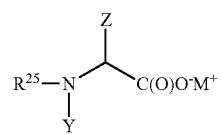

wherein $R^{25}$ represents a saturated or unsaturated hydrocarbon group having 10 to 22 carbon atoms or an acyl group containing a saturated or unsaturated hydrocarbon group having 9 to 22 carbon atoms, Y is hydrogen or methyl, Z is selected from hydrogen, —$CH_3$, —$CH(CH_3)_2$, —$CH_2CH(CH_3)_2$, —$CH(CH_3)CH_2CH_3$, —$CH_2C_6H_5$, —CH$_2$C$_6$H$_4$OH, —CH$_2$OH, —CH(OH)CH$_3$, —(CH$_2$)$_4$NH$_2$, —(CH$_2$)$_3$NHC(NH)NH$_2$, —CH$_2$C(O)O$^-$M$^+$, —(CH$_2$)$_2$ C(O)O$^-$M$^+$. M is a salt forming cation. In one aspect, R$^{25}$ represents a radical selected from a linear or branched C$_{10}$ to C$_{22}$ alkyl group, a linear or branched C$_{10}$ to C$_{22}$ alkenyl group, an acyl group represented by R$^{26}$C(O)—, wherein R$^{26}$ is selected from a linear or branched C$_9$ to C$_{22}$ alkyl group, a linear or branched C$_9$ to C$_{22}$ alkenyl group. In one aspect, M$^+$ is a cation selected from sodium, potassium, ammonium, and the ammonium salt of mono-, di, and triethanolamine (TEA).

The amino acid surfactants can be derived from the alkylation and acylation of α-amino acids such as, for example, alanine, arginine, aspartic acid, glutamic acid, glycine, isoleucine, leucine, lysine, phenylalanine, serine, tyrosine, and valine. Representative N-acyl amino acid surfactants are, but not limited to the mono- and di-carboxylate salts (e.g., sodium, potassium, ammonium and TEA) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and TEA) of N-acylated alanine, for example, sodium cocoyl alaninate, and TEA lauroyl alaninate; the carboxylate salts (e.g., sodium, potassium, ammonium and TEA) of N-acylated glycine, for example, sodium cocoyl glycinate, and potassium cocoyl glycinate; the carboxylate salts (e.g., sodium, potassium, ammonium and TEA) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate; and mixtures of the foregoing surfactants.

The betaines and sultaines useful in the present invention are selected from alkyl betaines, alkylamino betaines, and alkylamido betaines, as well as the corresponding sulfobetaines (sultaines) represented by the formulas:

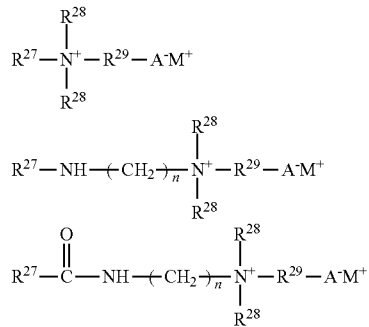

wherein R$^{27}$ is a C$_7$-C$_{22}$ alkyl or alkenyl group, each R$^{28}$ independently is a C$_1$-C$_4$ alkyl group, R$^{29}$ is a C$_1$-C$_5$ alkylene group or a hydroxy substituted C$_1$-C$_5$ alkylene group, n is an integer from 2 to 6, A is a carboxylate or sulfonate group, and M is a salt forming cation. In one aspect, R$^{27}$ is a C$_{11}$-C$_{18}$ alkyl group or a C$_{11}$-C$_{18}$ alkenyl group. In one aspect, R$^{28}$ is methyl. In one aspect, R$^{29}$ is methylene, ethylene or hydroxy propylene. In one aspect, n is 3. In a further aspect, M is selected from sodium, potassium, magnesium, ammonium, and mono-, di- and triethanolamine cations.

Examples of suitable betaines include, but are not limited to, lauryl betaine, coco betaine, oleyl betaine, coco hexadecyl dimethylbetaine, coco dimethyl carboxymethyl betaine, lauryl dimethyl carboxymethyl betaine, cetyl dimethyl carboxymethyl betaine, lauryl amidopropyl betaine, cocoamidopropyl betaine (CAPB), coco dimethyl sulfopropyl betaine, stearyl dimethyl sulfopropyl betaine, lauryl dimethyl sulfoethyl betaine, and cocamidopropyl hydroxysultaine.

The alkylamphocarboxylates such as the alkylamphoacetates and alkylamphopropionates (mono- and disubstituted carboxylates) can be represented by the formula:

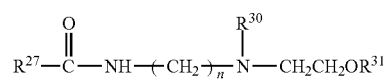

wherein R$^{27}$ is a C$_7$-C$_{22}$ alkyl or alkenyl group, R$^{30}$ is —CH$_2$C(O)O$^-$M$^+$, —CH$_2$CH$_2$C(O)O$^-$M$^+$, or —CH$_2$CH(OH)CH$_2$SO$_3^-$M$^+$, R$^{31}$ is hydrogen or —CH$_2$C(O)O$^-$M$^+$, and M is a cation selected from sodium, potassium, magnesium, ammonium, and the ammonium salt of mono-, di- and triethanolamine.

Exemplary alkylamphocarboxylates include, but are not limited to, sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate.

Non-limiting examples of nonionic surfactants are disclosed in *McCutcheon's Detergents and Emulsifiers*, North American Edition, 1998, supra; and McCutcheon's, *Functional Materials*, North American, supra; both of which are incorporated by reference herein in their entirety. Additional Examples of nonionic surfactants are described in U.S. Pat. No. 4,285,841, to Barrat et al., and U.S. Pat. No. 4,284,532, to Leikhim et al., both of which are incorporated by reference herein in their entirety. Nonionic surfactants typically have a hydrophobic portion, such as a long chain alkyl group or an alkylated aryl group, and a hydrophilic portion containing various degrees of ethoxylation and/or propoxylation (e.g., 1 to about 50) ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty acids, condensation products of ethylene oxide with long chain amines or amides, condensation products of ethylene oxide with alcohols, and mixtures thereof.

Suitable nonionic surfactants include, for example, alkyl polysaccharides, alcohol ethoxylates, block copolymers, castor oil ethoxylates, ceto/oleyl alcohol ethoxylates, cetearyl alcohol ethoxylates, decyl alcohol ethoxylates, dinonyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, monobranched alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, tallow oil fatty acid ethoxylates, tallow amine ethoxylates, tridecanol ethoxylates, acetylenic diols, polyoxyethylene sorbitols, and mixtures thereof. Various specific examples of suitable nonionic surfactants include, but are not limited to, methyl gluceth-10, PEG-20 methyl glucose distearate, PEG-20 methyl glucose sesquistearate, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, poloxamers such as poloxamer 188, polysorbate 21, polysorbate 40, polysorbate 60, polysorbate 61, polysorbate 65, polysorbate 80, polysorbate 81, polysorbate 85, sorbitan caprylate, sorbitan cocoate, sorbitan diisostearate, sorbitan dioleate, sorbitan distearate, sorbitan fatty acid ester, sorbitan isostearate, sorbitan laurate, sorbitan oleate, sorbitan palmitate, sorbitan sesquiisostearate, sorbitan sesquioleate, sorbitan sesquistearate, sorbitan stearate, sorbitan triisostearate, sorbitan trioleate, sorbitan tristearate, sorbitan undecylenate, or mixtures thereof.

Alkyl glycoside nonionic surfactants can also be employed and are generally prepared by reacting a monosaccharide, or a compound hydrolyzable to a monosaccharide, with an alcohol such as a fatty alcohol in an acid medium. For example, U.S. Pat. Nos. 5,527,892 and 5,770,543 describe alkyl glycosides and/or methods for their preparation. Suitable examples are commercially available under the names of Glucopon™ 220, 225, 425, 600 and 625, PLANTACARE®, and PLANTAPON®, all of which are available from Cognis Corporation of Ambler, Pa.

In another aspect, nonionic surfactants include, but are not limited to, alkoxylated methyl glucosides such as, for example, methyl gluceth-10, methyl gluceth-20, PPG-10 methyl glucose ether, and PPG-20 methyl glucose ether, available from Lubrizol Advanced Materials, Inc., under the trade names, Glucam® E10, Glucam® E20, Glucam® P10, and Glucam® P20, respectively; and hydrophobically modified alkoxylated methyl glucosides, such as PEG 120 methyl glucose dioleate, PEG-120 methyl glucose trioleate, and PEG-20 methyl glucose sesquistearate, available from Lubrizol Advanced Materials, Inc., under the trade names, Glucamate® DOE-120, Glucamate™ LT, and Glucamate™ SSE-20, respectively, are also suitable. Other exemplary hydrophobically modified alkoxylated methyl glucosides are disclosed in U.S. Pat. Nos. 6,573,375 and 6,727,357, the disclosures of which are hereby incorporated by reference in their entirety.

Other useful nonionic surfactants include water soluble silicones such as PEG-10 Dimethicone, PEG-12 Dimethicone, PEG-14 Dimethicone, PEG-17 Dimethicone, PPG-12 Dimethicone, PPG-17 Dimethicone and derivatized/functionalized forms thereof such as Bis-PEG/PPG-20/20 Dimethicone Bis-PEG/PPG-16/16 PEG/PPG-16/16 Dimethicone, PEG/PPG-14/4 Dimethicone, PEG/PPG-20/20 Dimethicone, PEG/PPG-20/23 Dimethicone, and Perfluorononylethyl Carboxydecyl PEG-10 Dimethicone.

The amount of the at least one anionic surfactant (active weight basis) utilized in formulating the cleansing compositions of the invention ranges from about 1 or 3 to about 22 wt. % based on the weight of the total composition. In another aspect, the amount of the at least one anionic surfactant utilized in the formulation of the cleansing composition ranges from about 3 to about 15 wt. %. In still another aspect, the amount of the at least one anionic surfactant employed in the cleansing composition ranges from about 5 to about 10 wt. %. In a further aspect, the amount of the at least one anionic surfactant utilized ranges from about 6 to about 9 wt. %. All weight percentages are based on the weight on the total weight of the cleansing composition.

In one embodiment of the invention, the weight ratio (based on active material) of anionic surfactant (non-ethoxylated and/or ethoxylated) to amphoteric surfactant can range from about 10:1 to about 2:1 in one aspect, and can be 9:1, 8:1, 7:1 6:1, 5:1, 4.5:1, 4:1, or 3:1 in another aspect. When employing an ethoxylated anionic surfactant in combination with a non-ethoxylated anionic surfactant and an amphoteric surfactant, the weight ratio (based on active material) of ethoxylated anionic surfactant to non-ethoxylated anionic surfactant to amphoteric surfactant can range from about 3.5:3.5:1 in one aspect to about 1:1:1 in another aspect.

In one aspect the optional anionic surfactant is selected from alkyl sulfates, including sodium lauryl sulfate, ammonium lauryl sulfate, sodium coco-sulfate, and mixtures thereof.

In one aspect the optional anionic surfactant is selected from ethoxylated alkyl sulfates including sodium laureth sulfate, ammonium laureth sulfate, sodium trideceth sulfate, and mixtures thereof.

In one aspect the optional amphoteric surfactant is selected from alkyl betaines, amidoalkyl betaines and amidoalkyl sultaines including lauryl betaine, cocamidopropyl betaine, cocamidopropyl hydroxysultaine, and mixtures thereof.

In one embodiment, the yield stress value of the cleansing composition containing the crosslinked nonionic, amphiphilic polymers of the invention is at least about 0.1 Pa in one aspect, about 0.5 Pa in one aspect, at least about 1 Pa in another aspect and at least about 1.5 Pa in a further aspect. In another embodiment, the yield stress of the cleansing composition ranges from about 0.1 to about 20 Pa in one aspect, from about 0.5 Pa to about 10 Pa in another aspect, from about 1 to about 3 Pa in a further aspect, and from about 1.5 to about 3.5 in a still further aspect.

Optionally, the cleansing and conditioning compositions of the invention can contain an electrolyte. Suitable electrolytes are known compounds and include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and blends thereof. The amount of the electrolyte used will generally depend on the amount of the amphiphilic polymer incorporated, but may be used at concentration levels of from about 0.1 to about 4 wt. % in one aspect, and from about 0.2 to about 2 wt. % in another aspect, based on the weight of the total composition.

The cleansing composition must be easily pourable with a shear thinning index of less than 0.5 at shear rates between 0.1 and 1 reciprocal second. The cleansing and compositions of the invention can be utilized in combination with an auxiliary rheology modifier (thickener) to enhance the yield value of a thickened liquid. In one aspect, the polymers of the invention can be combined with an auxiliary nonionic rheology modifier. In one aspect, an auxiliary nonionic rheology modifier to attain a desired yield stress value when a linear nonionic, amphiphilic polymer is utilized. Any rheology modifier is suitable including, but are not limited to, natural gums (e.g., polygalactomannan gums selected from fenugreek, cassia, locust bean, tara and guar), modified cellulose (e.g., ethylhexylethylcellulose (EHEC), hydroxybutylmethylcellulose (HBMC), hydroxyethylmethylcellulose (NEMC), hydroxypropylmethylcellulose (HPMC), methyl cellulose (MC), hydroxyethylcellulose (HEC), hydroxypropylcellulose (HPC) and cetyl hydroxyethylcellulose); and mixtures thereof methylcellulose, polyethylene glycols (e.g., PEG 4000, PEG 6000, PEG 8000, PEG 10000, PEG 20000), polyvinyl alcohol, polyacrylamides (homopolymers and copolymers), and hydrophobically modified ethoxylated urethanes (HEUR). The rheology modifier can be utilized in an amount ranging from about 0.5 to about 25 wt. % in one aspect, from about 1 to about 15 wt. % in another aspect, and from about 2 to about 10 wt. % in a further aspect, and from about 2.5 to about 5 wt. % based on the weight of the total weight of the composition.

The crosslinked, nonionic, amphiphilic polymers of the invention can be used in any cleansing or detersive application where enhanced foaming and yield stress properties are desired.

Water

The cleansing compositions of the invention are aqueous based systems comprising water as the carrier. The exact level of water will vary with the levels of the remaining components formulated into the composition. Generally, the cleansing compositions of the invention comprise from about 10 to about 95 wt. % in one aspect, from about 50 to about 92 wt. % in another aspect, and from about 60 to about 90 wt. % water in a further aspect.

In one embodiment, the crosslinked, nonionic, amphiphilic polymers of the invention can be utilized to enhance foaming properties and to stably suspend particulate materials and insoluble droplets within a surfactant containing cleansing and cleaning composition formulated for the personal care and home care industries.

In the personal care formulations, the crosslinked, nonionic, amphiphilic polymers of the invention can be utilized to enhance foaming properties, improve mildness and the yield stress properties of cleansing compositions for the hair and skin, and can be utilized for the stable suspension of insoluble silicones, opacifiers and pearlescent agents (e.g., mica, coated mica, ethylene glycol monostearate (EGMS), ethylene glycol distearate (EGDS), polyethylene glycol monostearate (PGMS) or polyethyleneglycol distearate (PGDS)), pigments, exfoliants, anti-dandruff agents, clay, swellable clay, laponite, gas bubbles, liposomes, microsponges, cosmetic beads, cosmetic microcapsules, and flakes, and are discussed in more detail below. The cleansing compositions may be in the form of a body wash, shower gel, bubble bath, two-in-one shampoo, conditioner, facial scrub, moisture rinse, make-up removal product, and the like.

Exemplary cosmetic bead components include, but are not limited to, agar beads, alginate beads, jojoba beads, gelatin beads, Styrofoam™ beads, polyacrylate, polymethylmethacrylate (PMMA), polyethylene beads, Unispheres™ and Unipearls™ cosmetic beads (Induchem USA, Inc., New York, N.Y.), Lipocapsule™, Liposphere™, and Lipopearl™ microcapsules (Lipo Technologies Inc., Vandalia, Ohio), and Confetti II™ dermal delivery flakes (United-Guardian, Inc., Hauppauge, N.Y.). Beads can be utilized as aesthetic materials or can be used to encapsulate benefit agents to protect them from the deteriorating effects of the environment or for optimal delivery, release and performance in the final product.

In one aspect, the cosmetic beads range in size from about 0.5 to about 1.5 mm. In another aspect, the difference in specific gravity of the bead and water is between about +/−0.01 and 0.5 in one aspect, and from about +/−0.2 to 0.3 g/ml in another aspect.

In one aspect, the microcapsules range in size from about 0.5 to about 300 μm. In another aspect, the difference in specific gravity between the microcapsules and water is from about +/−0.01 to 0.5. Non-limiting examples of microcapsule beads are disclosed in U.S. Pat. No. 7,786,027, the disclosure of which is herein incorporated by reference.

In one aspect of the invention, the amount of particulate component and/or insoluble droplets can range from about 0.1% to about 25 wt. % in one aspect, from about 0.5 to about 20 wt. % in another aspect, and from about 1 or 5 to about 10 wt. % in a further aspect, based on the total weight of the composition.

Other Optional Components

In addition to the components described above, the cleansing compositions may further comprise one or more other optional components that are known or otherwise suitable for use on the hair, scalp or skin and which do not interfere with the deposition properties of the composition. Non-limiting examples of such optional components are disclosed in the *International Cosmetic Ingredient Dictionary*, Fifth Edition, 1993, and the Cosmetic, Toiletry, and Fragrance Association (CTFA) *Cosmetic Ingredient Handbook*, Second edition, 1992, each of which are incorporated by reference. Exemplary optional components are disclosed below.

Silicone Conditioning Agents

The cleansing composition of the present invention optionally includes a silicone conditioning agent in the form of silicone particles or droplets. The silicone conditioning agent is intermixed in the composition so as to be in the form of dispersed, insoluble particles or droplets. In one aspect of the invention, the silicone oil can be in the form of preformed emulsified droplets or microemulsions.

The silicone conditioning agent may comprise volatile silicones, non-volatile silicones, and mixtures thereof. If volatile silicones are present, they are typically employed as a solvent or carrier for commercially available forms of non-volatile silicone fluid conditioning agents such as oils and gums. Volatile silicone fluids are often included in the conditioning package to improve silicone fluid deposition efficacy or to enhance the shine, sheen or glossiness of the hair. Volatile silicone materials are frequently included in formulations to enhance sensory attributes (e.g., feel) on the scalp and skin.

In one aspect, the silicone conditioning agent is non-volatile and insoluble in the aqueous personal care cleansing composition and includes silicone oils, gums, resins and mixtures thereof. By non-volatile is meant that the silicone has a very low vapor pressure at ambient temperature conditions (e.g., less than 2 mm Hg at 20° C.). The non-volatile silicone conditioning agent has a boiling point above about 250° C. in one aspect, above about 260° C. in another aspect, and above about 275° C. in a further aspect. Background information on silicones including sections discussing silicone oils, gums, and resins, as well as their manufacture, are found in *Encyclopedia of Polymer Science and Engineering*, vol. 15, 2d ed., pp 204-308, John Wiley & Sons, Inc. (1989).

The total concentration of silicone particles in the compositions of the present invention should be sufficient to provide the desired conditioning performance to the skin and hair, and generally ranges from about 0.01 to about 20 wt. % in one aspect, from about 0.05 to about 15 wt. % in another aspect, from about 0.1% to about 10 wt. % in still another aspect, and from about 1 to about 5 wt. % in a further aspect, based on the weight of the total composition.

The silicones used in the present invention have an average particle size or droplet size ranging from about 0.003 to about 500 μm in a first aspect, from about 0.05 to about 200 μm in a second aspect, from about 0.25 to about 200 μm in a third aspect, from about 0.5 to about 150 μm in a fourth aspect, from about 1 to about 100 μm in a fifth aspect, from about 5 to 80 μm in a sixth aspect, from about 10 to about 60 μm in an seventh aspect, and from about 20 to about 50 μm in an eighth aspect.

Silicone emulsions have an average silicone particle (droplet) size of less than 30 μm, less than 20 μm in another aspect, and less than 10 μm in a further aspect. In another aspect of the invention, the average silicone particle size of the silicone emulsion is less than 2 μm, and in another it ranges from 0.01 to 1 μm. Silicone emulsions having an average silicone particle (droplet) size of 0.15 μm or less are generally termed microemulsions and generally have an average particle size ranging from about 0.003 to about 0.15 μm.

The average particle size of the silicone conditioning agent particles can be measured by light scattering techniques well-known in the art for determining average particle size for emulsified liquids. One such method involves measuring particle size by means of a laser light scattering technique using a Horiba model LA 910 laser scattering particle size distribution analyzer (Horiba Instruments, Inc., Irvine, Calif.).

Silicone Oils

In one aspect, the silicone conditioning agent is silicone oil. In one aspect the silicone oil is a polyorganosiloxane material. The non-volatile silicone conditioning agents have a viscosity ranging from about above about 25 to about 1,000,000 mPa·s at 25° C. in one aspect, from about 100 to about 600,000 mPa·s in another aspect, and from about 1000 to about 100,000 mPa·s still another aspect, from about 2,000 to about 50,000 mPa·s in yet another aspect, and from about 4,000 to about 40,000 mPa·s in a further aspect. The viscosity is measured by means of a glass capillary viscometer as described by Dow Corning Corporate Test Method CTM004, dated Jul. 20, 1970. In one aspect the silicone oils have an average molecular weight below about 200,000 daltons. The average molecular weight can typically range from about 400 to about 199,000 daltons in one aspect, from about 500 to about 150,000 daltons in another aspect, from about 1,000 to about 100,000 daltons in still another aspect, from about 5,000 to about 65,000 daltons in a further aspect.

In one aspect, silicone oils suitable as conditioning agents are polyorganosiloxane materials selected from polyalkylsiloxanes, polyarylsiloxanes, polyalkylarylsiloxanes, hydroxyl terminated polyalkylsiloxanes, polyarylalkylsiloxanes, amino functional polyalkylsiloxanes, quaternary functional polyalkylsiloxanes, and mixtures thereof.

In one aspect, the silicone conditioning agent includes polyorganosiloxanes represented by Formula X:

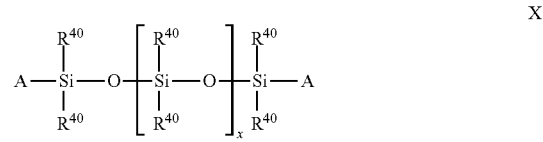

wherein A independently represents hydroxy, methyl, methoxy, ethoxy, propoxy, and phenoxy; $R^{40}$ independently represents methyl, ethyl, propyl, phenyl, methylphenyl, phenylmethyl, a primary, secondary or tertiary amine, a quaternary group selected from a group selected from:

—$R^{41}$—$N(R^{42})CH_2CH_2N(R^{42})_2$;
—$R^{41}$—$N(R^{42})_2$;
—$R^{41}$—$N^+(R^{42})_3CA^-$; and
—$R^{41}$—$N(R^{42})CH_2CH_2N(R^{42})H_2CA^-$ wherein $R^{41}$ is a linear or branched, hydroxyl substituted or unsubstituted alkylene or alkylene ether moiety containing 2 to 10 carbon atoms; $R^{42}$ is hydrogen, $C_1$-$C_{20}$ alkyl (e.g, methyl), phenyl or benzyl; q is an integer ranging from about 2 to about 8; $CA^-$ is a halide ion selected from chlorine, bromine, iodine and fluorine; and x is an integer ranging from about 7 to about 8000 in one aspect, from about 50 to about 5000 in another aspect, form about 100 to about 3000 in still another aspect, and from about 200 to about 1000 in a further aspect.

In one aspect, the amino functional silicone is represented by Formula XA:

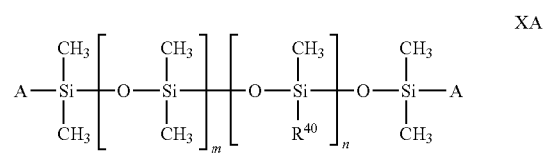

wherein A independently represents hydroxy, methyl, methoxy, ethoxy, propoxy, and phenoxy; and $R^{40}$ is selected from:

—$R^{41}$—$N(R^{42})CH_2CH_2N(R^{42})_2$;
—$R^{41}$—$N(R^{42})_2$;
—$R^{41}$—$N^+(R^{42})_3CA^-$; and
—$R^{41}$—$N(R^{42})CH_2CH_2N(R^{42})H_2CA^-$ wherein $R^{41}$ is a linear or branched, hydroxyl substituted or unsubstituted alkylene or alkylene ether moiety containing 2 to 10 carbon atoms; $R^{42}$ is hydrogen, $C_1$-$C_{20}$ alkyl (e.g, methyl), phenyl or benzyl; $CA^-$ is a halide ion selected from chlorine, bromine, iodine and fluorine; and the sum of m+n ranges from about 7 to about 1000 in one aspect, from about 50 to about 250 in another aspect, and from about 100 to about 200 in another aspect, subject to the proviso that m or n is not 0. In one aspect A is hydroxy and $R^{40}$ is —$(CH_2)_3$NH$(CH_2)_3$NH$_2$. In another aspect A is methyl and $R^{40}$ is —$(CH_2)_3$NH$(CH_2)_3$NH$_2$. In still another aspect A is methyl and $R^{40}$ is a quaternary ammonium moiety represented by —$(CH_2)_3OCH_2CH(OH)CH_2N^+(R^{42})_3CA^-$; wherein $R^{42}$ and $CA^-$ are as previously defined.

Exemplary silicone oil conditioning agents include, but are not limited to, polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxanes (amodimethicones), and mixtures thereof.

Silicone Gums

Another silicone conditioning agent useful in the invention is a silicone gum. A silicone gum is a polyorganosiloxane material of the same general structure of the silicone oils set forth under Formula XII wherein A independently represents hydroxy, methyl, methoxy, ethoxy, propoxy, and phenoxy; $R^{40}$ independently represents methyl, ethyl, propyl, phenyl, methylphenyl, phenylmethyl, and vinyl. Silicone gums have a viscosity measured at 25° C. of greater than 1,000,000 mPa·s. The viscosity can be measured by means of a glass capillary viscometer as described above for the silicone oils. In one aspect the silicone gums have an average molecular weight about 200,000 daltons and above. The molecular weight can typically range from about 200,000 to about 1,000,000 daltons. It is recognized that the silicone gums described herein can also have some overlap with the silicone oils described previously. This overlap is not intended as a limitation on any of these materials.

Suitable silicone gums for use in the silicone component of compositions of the invention are polydimethylsiloxanes (dimethicones), optionally having terminal end groups such as hydroxyl (dimethiconols), polymethylvinylsiloxane, polydiphenylsiloxane, and mixtures thereof.

Silicone Resins

Silicone resins can be included as a silicone conditioning agent suitable for use in the compositions of the present invention. These resins are crosslinked polysiloxanes. The crosslinking is introduced through the incorporation of trifunctional and tetrafunctional silanes with monofunctional and/or difunctional silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they form a rigid or hard film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. In one aspect, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl substituted silanes being most commonly utilized.

Silicone materials and silicone resins can be identified according to a shorthand nomenclature system known to those of ordinary skill in the art as "MDTQ" nomenclature. Under this naming system, the silicone is described according to the presence of various siloxane monomer units which make up the silicone. The "MDTQ" nomenclature system is described in the publication entitled "*Silicones: Preparation, Properties and Performance*"; Dow Corning Corporation, 2005, and in U.S. Pat. No. 6,200,554.

Exemplary silicone resins for use in the compositions of the present invention include, but are not limited to MQ, MT, MTQ, MDT and MDTQ resins. In one aspect, methyl is the silicone resin substituent. In another aspect, the silicone resin is selected from a MQ resins, wherein the M:Q ratio is from about 0.5:1.0 to about 1.5:1.0 and the average molecular weight of the silicone resin is from about 1000 to about 10,000 daltons.

Volatile Silicones

The optional volatile silicones referred to above include linear and cyclic polydimethylsiloxanes (cyclomethicones), and mixtures thereof. The term "volatile" means that the silicone has a measurable vapor pressure, or a vapor pressure of at least 2 mm of Hg at 20° C. The volatile silicones have a viscosity of 25 mPa·s or less at 25° C. in one aspect, from about 0.65 about to about 10 mPa·s in another aspect, from about 1 to about 5 mPa·s in still another aspect, and from about 1.5 to about 3.5 mPa·s in a further aspect. A description of linear and cyclic volatile silicones is found in Todd and Byers, "Volatile Silicone Fluids for Cosmetics", Cosmetics and Toiletries, Vol. 91(1), pp. 27-32 (1976), and in Kasprzak, "Volatile Silicones", Soap/Cosmetics/Chemical Specialities, pp. 40-43 (December 1986).

The linear volatile silicones are silicone fluids, as described above in Formula XII but having viscosities of not more than about 25 mPa·s. The cyclomethicones typically contain about 3 to about 7 dimethyl substituted silicon atoms in one aspect and from about 3 to about 5 in another aspect, alternating with oxygen atoms, in a cyclic ring structure.

Conditioning Oils

A further component that may be used in the compositions of the invention is a conditioning oil (other than a silicone) selected from a hydrocarbon oil or an ester oil. These auxiliary conditioning agent materials may enhance the conditioning benefits of the silicone materials used in the cleansing compositions of the invention.

Suitable hydrocarbon oils have at least 12 carbon atoms, and include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched chain isomers of these compounds, as well as of higher chain length hydrocarbons, can also be used. Also suitable are polymeric hydrocarbons of $C_2$-$C_6$ alkenyl monomers, such as polyisobutylene.

Suitable ester oils have at least 10 carbon atoms, and include esters with hydrocarbyl chains derived from fatty acids or alcohols. In one aspect the ester oils conform to the formula ITC(O)OR in which R' and R independently represent alkyl or alkenyl radicals and the sum of carbon atoms in R' and R is at least 10 in one aspect, and at least 20 in another aspect. Dialkyl and trialkyl and alkenyl esters of polycarboxylic acids can also be used.

In another aspect ester oils are fatty esters of mono-, di- and triglycerides, more specifically the mono-, di-, and tri-esters of glycerol derived from long chain carboxylic acids such as $C_1$-$C_{22}$ carboxylic acids. Examples of such materials include cocoa butter, palm stearin, sunflower oil, soybean oil and coconut oil.

Mixtures of any of the above described hydrocarbon and ester oils also can be used. The total combined amount of hydrocarbon oil and/or ester oil in compositions of the invention may suitably range from about 0.05 to about 10 wt. % in one aspect, from about 0.2 to about 5 wt. %, and especially from about 0.5 to about 3 wt. % based on the weight of the total composition.

Cationic Polymers

Cationic polymers are components that can enhance the delivery of conditioning agents and/or provide auxiliary conditioning benefits to the hair, scalp or skin to improve and enhance the conditioning benefits delivered by the silicone conditioning agents of the invention. Cationic polymer refers to polymers containing at least one cationic moiety or at least one moiety that can be ionized to form a cationic moiety. Typically, these cationic moieties are nitrogen containing groups such as quaternary ammonium or protonated amino groups. The cationic protonated amines can be primary, secondary, or tertiary amines. The cationic polymer typically has a cationic charge density ranging from about 0.2 to about 7 meq/g at the pH of the intended use of the composition. The average molecular weight of the cationic polymer ranges from about 5,000 daltons to about 10,000,000 daltons.

Non-limiting examples of such polymers are described in the CTFA *International Cosmetic Ingredient Dictionary/Handbook* via the CTFA website as well as the CTFA *Cosmetic Ingredient Handbook*, Ninth Ed., Cosmetic and Fragrance Assn., Inc., Washington D.C. (2002), incorporated herein by reference, can be used.

Non-limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (CTFA, Polyquaternium-16); copolymers of 1-vinyl-2-pyrrolidone and dimethylaminoethyl methacrylate (CTFA, Polyquaternium-11); cationic diallyl quaternary ammonium-containing polymers, including, for example, dimethyldiallylammonium chloride homopolymer, copolymers of acrylamide and dimethyldiallylammonium chloride (CTFA, Polyquaternium-6 and Polyquaternium-7, respectively); amphoteric copolymers of acrylic acid including copolymers of acrylic acid and dimethyldiallylammonium chloride (CTFA, Polyquaternium-22); terpolymers of acrylic acid with dimethyldiallylammonium chloride and acrylamide (CTFA, Polyquaternium-39); terpolymers of acrylic acid with methacrylamidopropyl trimethylammonium chloride and methylacrylate (CTFA, Polyquaternium-47); terpolymers of acrylic acid, methacrylamidopropyl trimethylammonium chloride and acrylamide (CTFA, Polyquaternium-53). In one aspect, suitable cationic substituted monomers are the cationic substituted dialkylaminoalkyl acrylamides, dialkylaminoalkyl methacrylamides, and combinations thereof.

Other suitable cationic polymers for use in the composition include polysaccharide polymers, such as cationic cellulose derivatives and cationic starch derivatives modified with a quaternary ammonium halide moiety. Exemplary cationic cellulose polymers are salts of hydroxyethyl cellulose reacted with trimethyl ammonium substituted epoxide (CTFA, Polyquaternium-10). Other suitable types of cationic cellulose include the polymeric quaternary ammonium salts of hydroxyethyl cellulose reacted with lauryl dimethyl ammonium substituted epoxide (CTFA, Polyquaternium-24).

Other suitable cationic polymers include cationic polygalactomannan derivatives such as guar gum derivatives and cassia gum derivatives, e.g., guar hydroxypropyltrimonium chloride, hydroxypropyl hydroxypropyltrimonium chloride guar and cassia hydroxypropyltrimonium chloride, respectively. Guar hydroxypropyltrimonium chloride is commercially available under the Jaguar™ trade name series from Rhodia Inc. and the N-Hance trade name series from Ashland Inc. Cassia hydroxypropyltrimonium chloride is commercially available under the Sensomer™ trade name series from Lubrizol Advanced Materials, Inc.

The amount of cationic polymer that may be utilized in the cleansing compositions of the invention range from about 0.01 to about 10 wt. % in one aspect, from about 0.05 to about 3 wt. % in another aspect, and from about 0.1 to about 1 wt. % in a further aspect, based on the weight of the total composition.

Pigments

Exemplary pigments are metal compounds or semi metallic compounds and may be used in ionic, nonionic or oxidized form. The pigments can be in this form either individually or in admixture or as individual mixed oxides or mixtures thereof, including mixtures of mixed oxides and pure oxides. Examples are the titanium oxides (e.g., $TiO_2$), zinc oxides (e.g., ZnO), aluminum oxides (for example, $Al_2O_3$), iron oxides (for example, $Fe_2O_3$), manganese oxides (e.g., MnO), silicon oxides (e.g., $SiO_2$), silicates, cerium oxides, zirconium oxides (e.g., $ZrO_2$), barium sulfate ($BaSO_4$), nylon-12, and mixtures thereof.

Other examples of pigments include thermochromic dyes that change color with temperature, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide nanoparticles, barium oxide, ultramarine blue, bismuth citrate, hydroxyapatite, zirconium silicate, carbon black particles, and the like.

If utilized, the amount of pigment employed in the formulation should be sufficient to provide the desired product aesthetic effect and is well within the skill in the formulation art. In one aspect the amount of pigment typically utilized in the compositions of the invention range from about 0.5 wt. % to about 20 wt. % in one aspect, from about 1 to about 15 wt. % in another aspect, and from about 5 to about 10 wt. % in a further aspect, based on the total weight of the composition.

Exfoliating Agents

Cosmetically useful particulate exfoliating agents are known in the art, and the selection and amount is determined by the exfoliating effect desired from the use of the composition, as recognized by those skilled in the cosmetic arts. Useful exfoliating agents include, but are not limited to, natural abrasives, inorganic abrasives, synthetic polymers, and the like, and mixtures thereof. Representative exfoliants include, but are not limited to, ground or powdered pumice, stone, zeolites, nut shells (e.g., almond, pecan, walnut, coconut, and the like), nut meals (e.g., almond, and the like), fruit pits (e.g., apricot, avocado, olive, peach, and the like), hulls, seed and kernel (e.g., oat bran, corn meal, rice bran, grape seed, kiwi seed, wheat, jojoba seed, loofah seed, rose hip seed, and the like), plant matter (e.g., tea tree leaves, corn cob, fruit fibers, seaweed, loofah sponge, microcrystalline cellulose, and the like), bivalve shells (oyster shell, and the like), diatomaceous earth, calcium carbonate, dicalcium pyrophosphate, chalk, silica, kaolin clay, silicic acid, aluminum oxide, stannic oxide, sea salt (e.g., Dead Sea salt), talc, sugars (e.g., table, brown, and the like), polyethylene, polystyrene, microcrystalline polyamides (nylons), microcrystalline polyesters, polycarbonates, and stainless steel fibers. The foregoing exfoliants can be used in the form of granules, powders, flours, and fibers.

The exfoliating agents for use in the present invention include inorganic physical abrasive type exfoliating agents, a number of which are presented above. In this aspect of the present invention, the exfoliating agent comprises from about 0.1 to about 20 wt. % in one aspect, and from about 0.5 to about 10 wt. % in another aspect, based on the weight of the composition.

Anti-Dandruff Agents

Any suitable anti-dandruff agent can be employed in the compositions of the present invention. The anti-dandruff agents may be insoluble or water soluble. Exemplary anti-dandruff agents include, but are not limited to, sulfur, zinc pyrithione, zinc omadine, miconazole nitrate, selenium sulfide, piroctone olamine, N,N-bis(2-hydroxyethyl)undecenamide, cade oil, pine tar, *Allium cepa* extract *Picea abies* extract, and Undecyleneth-6, and the like, and mixtures thereof.

In one aspect of the invention, the anti-dandruff agents can be incorporated into the cleansing composition in an amount ranging from about 0.001 to about 10 wt. % in one aspect, from about 0.1 to about 5 wt. % in another aspect, and from about 0.5 to about 3 wt. % in a further aspect, based on the total weight of the stabilized composition.

Pearlescent/Opacifying Agents

Some formulations are often opacified by deliberately incorporating pearlescent materials therein to achieve a cosmetically attractive pearl-like appearance, known as pearlescence. An opacifier often is included in a composition to mask an undesirable aesthetic property, such as to improve the color of a composition that is darkened due to the presence of a particular ingredient, or to mask the presence of a particulate material in the composition. Opacifiers also are included in aqueous compositions to improve the aesthetics and consumer acceptance of an otherwise esthetically unpleasing composition. For example, an opacifier can impart a pearlescent appearance to a clear composition, thereby communicating an appearance of creaminess, mildness and body to the consumer. Persons skilled in the art are aware of problems faced by formulators in consistently preparing a stable pearlescent formulation. A detailed discussion is found in the article "Opacifiers and pearling agents in shampoos" by Hunting, *Cosmetic and Toiletries*, Vol. 96, pages 65-78 (July 1981), incorporated herein by reference.

The opacifying or pearlescent material includes organic compounds and inorganic compounds. Typical examples of organic compounds are monoesters and/or diesters of ethylene glycol, propylene glycol, diethylene glycol, dipropylene glycol, triethylene glycol or tetraethylene glycol with fatty acids containing from about 6 to about 22 carbon atoms in one aspect, and from about 12 to about 18 carbon atoms in another aspect. Such fatty acids include caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid, erucic acid, and mixtures thereof. In one aspect, ethylene glycol monostearate (EGMS) and/or ethylene glycol distearate (EGDS) and/or polyethylene glycol monostearate (PGMS) and/or polyethyleneglycol distearate (PGDS) are suitable pearlescent agents used in the composition.

Inorganic pearlescent agents include those selected from the group consisting of mica, metal oxide coated mica, silica coated mica, bismuth oxychloride coated mica, bismuth oxychloride, myristyl myristate, glass, metal oxide coated glass, various aluminum and magnesium salts, guanine, fish scales, glitter (polyester or metallic) and mixtures thereof.

Suitable micas include muscovite or potassium aluminum hydroxide fluoride. The platelets of mica are can be coated with a thin layer of metal oxide. Metal oxides are selected from the group consisting of rutile, titanium dioxide, ferric oxide, tin oxide, alumina and mixtures thereof.

A representative listing of opacifiers is found in the CTFA *Cosmetic Ingredient Handbook*, J. Nikitakis, ed., 1988, at page 75. Other pearlescent or opacifying materials are disclosed in U.S. Pat. No. 4,654,207; U.S. Pat. No. 5,019,376; and U.S. Pat. No. 5,384,114; which are herein incorporated by reference.

In one aspect, the amount of the pearlescent or opacifying material can be used in amounts ranging from about 0.01 to about 10 wt. % in one aspect, from about 0.1% to about 5 wt. % in another aspect, and from 0.5 to about 3 wt. % in a further aspect, based upon the total weight of the composition.

Additional optional components for inclusion in the compositions of the invention the following may be mentioned: fragrances, chelating agents, auxiliary suspending agents and viscosity modifiers, such as guar and xanthan gums, emulsifiers, preservatives, amino acids, peptides, proteins, provitamins such as panthenol, vitamins, herb and plant extracts, humectants such as glycerine, and mixtures thereof.

The amount of these additives range from about 0 to about 20 wt. % in one aspect, from about 0.1 to about 10 wt. %, and from about 0.5 to about 5 wt. %, based on the total weight of the composition. The amount of each additive is readily determined by one skilled in the formulation art, depending on the nature and intended function for the additive.

The personal care cleansing compositions of the invention may be formulated as a body wash, shower gel, bubble bath, two-in-one shampoo, conditioner, facial scrub, moisture rinse, make-up removal product, and the like. The cleansers can be used, for example, for washing hair, skin, eyelashes, eyebrows, nails, lips, face, or the scalp. The compositions are applied topically to the desired area of the skin or hair in an amount sufficient to provide effective cleansing via the use of a cleansing puff, washcloth, sponge or other preferred consumer scrubbing implement. The compositions are preferably diluted with water prior to, during, or after topical application, and then subsequently rinsed off of the applied area using water.

The present invention may also be useful in rinse-off applications other than personal care compositions including pet care, auto care, home care and medical applications.

Shampoo embodiments of the invention can be formulated as two-in-one shampoos, baby shampoos, conditioning shampoos, bodifying shampoos, moisturizing shampoos, temporary hair color shampoos, three-in-one shampoos, anti-dandruff shampoos, hair color maintenance shampoos, acid (neutralizing) shampoos, medicated shampoos, and salicylic acid shampoos, and the like.

Liquid Fatty Acid Soap Based Cleansers

In one aspect, a personal care cleansing composition in which the polymer of this invention is useful is a fatty acid soap based cleanser. Typical components of a fatty acid based soap cleanser, in addition to the crosslinked, nonionic, amphiphilic polymers of the invention are: at least one fatty acid salt; water, an optional surfactant or mixture of surfactants; a sufficient amount of a pH adjusting agent (base and/or acid) to attain a pH of above 7 in one aspect, from about 7.5 to about 14 in another aspect, from about 8 to about 12 in still another aspect, and from about 8.5 to about 10 in a further aspect. Optional ingredients may be included such as the adjuvants, additives and benefit agents discussed above, and mixtures thereof, including silicones, conditioning oils, cationic polymers, particulates and insoluble materials (e.g., pigments, anti-dandruff agents, pearlescent materials, opacifying materials, gas bubbles, cosmetic beads, flakes, and capsules), fragrances, chelating agents, auxiliary suspending agents and viscosity modifiers, emulsifiers, preservatives, amino acids, peptides, proteins, provitamins, vitamins, herb and plant extracts, humectants, and mixtures thereof.

In one aspect, the fatty acid soaps are selected from at least one the fatty acid salt (e.g., sodium, potassium, and ammonium) containing from about 8 to about 22 carbon atoms. In another aspect of the invention, the liquid soap composition contains at least one fatty acid salt containing from about 12 to about 18 carbon atoms. The fatty acids utilized in the soaps can be saturated and unsaturated and can be derived from synthetic sources, as well as from the saponification of fats and natural oils by a suitable base (e.g., sodium, potassium and ammonium hydroxides). Exemplary saturated fatty acids include but are not limited to octanoic, decanoic, lauric, myristic, pentadecanoic, palmitic, margaric, steric, isostearic, nonadecanoic, arachidic, behenic, and the like, and mixtures thereof. Exemplary unsaturated fatty acids include but are not limited to the salts (e.g., sodium, potassium, ammonium) of myristoleic, palmitoleic, oleic, linoleic, linolenic, and the like, and mixtures thereof. The fatty acids can be derived from animal fat such as tallow or from vegetable oil such as coconut oil, red oil, palm kernel oil, palm oil, cottonseed oil, olive oil, soybean oil, peanut oil, corn oil, and mixtures thereof. The amount of fatty acid soap (active weight basis) that can be employed in the liquid cleansing compositions of this embodiment ranges from about 1 or 3 to about 22 wt. % in one aspect, from about 3 to about 15 wt. % in another aspect, from about 5 to 10 wt. % in a further aspect, and from 6 to about 9 wt. % in still a further aspect, based on the weight of the total composition.

The optional anionic surfactant can be present in the soap composition in an amount ranging from about 1 to about 9 wt. % in one aspect, and from about 6 to about 9 wt. % in another aspect, based on the total weight of the soap composition. Mixtures of anionic and amphoteric surfactants can be used. In one embodiment of the invention, the weight ratio (based on active material) of anionic surfactant (non-ethoxylated and/or ethoxylated) to amphoteric surfactant can range from about 10:1 to about 2:1 in one aspect, and can be 9:1, 8:1, 7:1 6:1, 5:1, 4.5:1, 4:1, or 3:1 in another aspect. When employing an ethoxylated anionic surfactant in combination with a non-ethoxylated anionic surfactant and an amphoteric surfactant, the weight ratio (based on active material) of ethoxylated anionic surfactant to non-ethoxylated anionic surfactant to amphoteric surfactant can range from about 3.5:3.5:1 in one aspect to about 1:1:1 in another aspect.

In one aspect, the optional anionic surfactant is selected from alkyl sulfates, including sodium lauryl sulfate, ammonium lauryl sulfate, sodium coco-sulfate, and mixtures thereof.

In one aspect, the optional anionic surfactant is selected from ethoxylated alkyl sulfates including sodium laureth sulfate, ammonium laureth sulfate, sodium trideceth sulfate, and mixtures thereof.

In one aspect, the optional amphoteric surfactant is selected from alkyl betaines, amidoalkyl betaines and amidoalkyl sultaines including lauryl betaine, cocamidopropyl betaine, cocamidopropyl hydroxysultaine, and mixtures thereof.

In the foregoing soap embodiments of the invention, the amount of the crosslinked, nonionic, amphiphilic polymer can range from about 0.5% to about 5% by weight in one aspect, from about 1% to about 3% by weight in another aspect, and from about 1.5% to about 2.5% by weight in a further aspect, based on the total weight of the soap composition.

The liquid fatty acid soap based cleanser embodiments of the invention can be formulated as body washes, bath gels, shower gels, liquid hand soaps, body scrubs; bubble baths, facial scrubs, and foot scrubs, two-in-one shampoos, baby shampoos, conditioning shampoos, bodifying shampoos, moisturizing shampoos, temporary hair color shampoos, three-in-one shampoos, anti-dandruff shampoos, hair color maintenance shampoos, acid (neutralizing) shampoos, medicated shampoos, and salicylic acid shampoos, and the like.

Advantageously, the nonionic, amphoteric polymer component of the invention is not pH dependent so the relatively high (basic) pH needed to maintain the fatty acid soap in liquid form does not affect the rheological properties imparted by the polymer.

Multi-Phase Appearance

Visually distinct, multiple phase compositions where one phase is clear and another phase is opaque or pearlized are also envisioned. In one embodiment of the invention, a pattern comprising phases that are visually distinct from each other may be formed by mixing clear and opaque and/or pearlescent components. The visual distinction between each phase can be in color, texture, density, and the type of insoluble component contained therein. The specific pattern can be chosen from a wide variety of patterns, including, but not limited to the following examples: striped, marbled, rectilinear, interrupted striped, check, mottled, marbled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, and tessellated. The pattern results from the combination of the "multi-phase" composition by a method of manufacture described in U.S. Pat. No. 6,213,166 (Thibiant et al.), U.S. Patent Publication No. US 2004/0219119 (Wei et al.), and U.S. Patent Publication No. US2011/0117225 (Wei et al.), which are herein incorporated by reference.

By the term "multi-phase" as used herein, is meant that each phase of the present compositions occupy separate but distinct physical spaces inside the package in which they are stored, but are in direct contact with one another (i.e., they are not separated by a barrier and they are not emulsified or mixed to any significant degree). In one embodiment of the present invention, the "multi-phase" compositions comprise at least two visually distinct phases, which are present within the container as a visually distinct pattern.

Each visually distinct phase can also include different insoluble materials and/or particulates such as pigments, cosmetic beads, cosmetic flakes, mica, air bubbles, exfoliants, pearlescent materials, opacifiers, silicones, botanicals, benefit agents, and the like as described herein and in the art.

Compositions of this invention demonstrate excellent stability with time in suspending insoluble components and/or benefit agents and stabilizing the visually distinct phases. Multiple-phase compositions are disclosed in U.S.

Published Patent Application Nos. 2006/0079417, 2006/0079418, 2006/0079419, 2006/0079420, 2006/0079421, 2006/0079422, 2007/0009463, 2007/0072781, 2007/0280976, and 2008/0317698 to the Procter and Gamble Company, which are herein incorporated by reference.

Desirably, the stable multi-phase embodiments of the invention comprise at least two visually distinct phases that are packaged in a transparent or translucent container or package such that the consumer can view the pattern through the container or package.

This invention is illustrated by the following examples that are merely for the purpose of illustration and are not to be regarded as limiting the scope of the invention or the manner in which it can be practiced. Unless specifically indicated otherwise, parts and percentages are given by weight.

Test Methods

Foam Volume Testing

Experiments relating to the foaming behavior of cleansing compositions (e.g., shampoo formulations) are carried out on a SITA model R-2000 foam tester interfaced with a personal computer equipped with data acquisition and analysis software (SITA-foam software DAC/DL), SITA Messtechnik GmbH (Dresden, Germany). Brochures, schematic diagrams, and foam testing protocols for the SITA Foam Tester (model R-2000) instrument are available online at: (http://www.online-tensiometer.com/produkte/r2000/foam_tester_r2000.html), which is herein incorporated by reference.

The SITA Foam Tester utilizes a patented rotor of defined geometry for foam generation. The rotor mechanically inserts air bubbles into the test sample. The generated foam volume is measured by an array of sensor needles, which scan the foam surface. The array of sensor needles permits exact measurement of the generated foam volume even with uneven foam surfaces. The output is given as average ml of foam volume per measure.

A stock shampoo test formulation containing the cross-linked, nonionic, amphiphilic polymer of the invention is prepared by diluting 5 g of the test shampoo with simulated tap water (the hard dilution water is prepared by dissolving 0.74 g of $MgSO_4$ and 1.324 g of $CaCl_2$ in 1 L of D.I. water (hardness level 1,517.35 mg/L) to a final concentration of 0.5 wt. % (5 g test shampoo diluted in 100 g hard water mixed with 895 g deionized (D.I.) water). The diluted stock shampoo test formulation is carefully dispensed into the reservoir tank of the SITA Foam Tester to avoid any foam formation. The stock formulation is allowed to equilibrate so that any air bubbles formed during the reservoir filling migrate to the surface. The diluted shampoo test sample (300 ml) is automatically withdrawn from the bottom of the reservoir tank and introduced into a temperature controlled foam generation test vessel and allowed to equilibrate at 40° C. (±1° C.). The test sample is agitated by the rotor at 1000 rpm for 20 sec. and the foam volume is measured and recorded. The agitation/measurement cycle is repeated 40 times with a rest interval between cycles of 30 sec. Two runs for each test sample is conducted and the average foam volume for both runs is recorded.

Yield Stress Measurement

The yield stress of these polymers are determined by oscillatory and steady shear measurements on a controlled stress rheometer (TA Instruments AR1000N rheometer, New Castle, Del.) with parallel plate geometry (40 mm stainless steel plate and 1000 μm gap) at 25° C. The oscillatory measurements are performed at a fixed frequency of 1 radian/sec. The elastic and viscous moduli (G' and G" respectively) are obtained as a function of increasing stress amplitude. In cases where the swollen polymer particles create a jammed network, G' is larger than G" at low stress amplitudes but decreases at higher amplitudes crossing G" because of rupture of the network. The stress corresponding to the crossover of G' and G" is noted as the yield stress.

Viscosity (Brookfield)

Brookfield rotating spindle method (all viscosity measurements reported herein are conducted by the Brookfield method whether mentioned or not): The viscosity measurements are calculated in mPa·s, employing a Brookfield rotating spindle viscometer, Model RVT (Brookfield Engineering Laboratories, Inc.), at about 20 revolutions per minute (rpm), at ambient room temperature of about 20 to 25° C. (hereafter referred to as viscosity). Spindle sizes are selected in accordance with the standard operating recommendations from the manufacturer. Generally, spindle sizes are selected as follows:

| Spindle Size No. | Viscosity Range (mPa · s) |
|---|---|
| 1 | 1-50 |
| 2 | 500-1,000 |
| 3 | 1,000-5,000 |
| 4 | 5,000-10,000 |
| 5 | 10,000-20,000 |
| 6 | 20,000-50,000 |
| 7 | >50,000 |

The spindle size recommendations are for illustrative purposes only. The artisan of ordinary skill in the art will select a spindle size appropriate for the system to be measured.

ABBREVIATIONS

The following abbreviations and trade names are utilized in the examples.

Abbreviations and Trade Names

| Abbreviation | Chemical Name |
|---|---|
| VA | Vinyl acetate |
| SMA | Stearyl methacrylate |
| BEM | Behenyl ethoxylated-25 methacrylate |
| NVP | N-vinyl-2-pyrrolidone (N-vinyl pyrrolidone) |
| VA-10 | Vinyl neodecanoate |
| APE | Allyl pentaerythritol |
| CYCLO | Cyclohexane |
| EA | Ethyl Acetate |

| Abbreviation | Chemical Name |
|---|---|
| PGS | Reaction product $C_{20}$-$C_{24}$ substituted succinic anhydride and glycerin and or polyglycerol containing 2 to 6 glycerin units utilized as a process aid |
| Sulfochem™ ES-2 CWK anionic surfactant (28% active) | Sodium Laureth-2 sulfate (Lubrizol Advanced Materials, Inc.) |
| Sulfochem™ ALS (30% active) | Ammonium Lauryl Sulfate anionic surfactant (Lubrizol Advanced Materials, Inc.) |
| Chembetaine™ CAD amphoteric surfactant (35% active) | Cocamidopropylbetaine (Lubrizol Advanced Materials, Inc.) |
| Chembetaine™ C amphoteric surfactant (35% active) | Cocamidopropylbetaine (Lubrizol Advanced Materials, Inc.) |
| Dow Corning® DC 2-1352 silicone emulsion (60% active) | INCI Name[1]: Dimethicone (and) Laureth-23 (and) C12-15 Pareth-3 (Dow Corning Corporation) (0.5 μm) |
| Jaguar® C13-S cationic guar | Guar Hydroxypropyltrimonium Chloride (Rhodia Group) |
| Glydant® Plus preservative (2.0 w/w aqueous solution) | DMDM Hydantoin (and) Iodopropynyl Butylcarbamate (Lonza Group Ltd.) |
| Carbopol® 980 polymer | INCI Name: Carbomer. A homopolymer of acrylic acid crosslinked with an allyl ether of pentaerythritol, an allyl ether of sucrose, or an allyl ether of propylene (Lubrizol Advanced Materials, Inc.) |

[1]INCI name is the International Nomenclature Cosmetic Ingredient name assigned to a cosmetic ingredient by the International Nomenclature Committee of the Cosmetic, Toiletry, and Fragrance Association (CTFA), Washington, DC, USA, now known as the Personal Care Products Council (PCPC). INCI Names and their definitions are published in the International Cosmetic Ingredient Dictionary and Handbook.

Examples 1-9 (Polymer Synthesis)

A free radical initiated dispersion polymerization is utilized to prepare the nonionic, amphiphilic polymer component of the invention. The polymerization reactor consists of a water-cooled resin kettle equipped with a reflux condenser, nitrogen purging tube, a mechanical agitator and a thermalcouple connected to a temperature control module. Admixtures of monomers, crosslinkers, and processing aids set forth in Table 1 are added to the resin kettle, followed by the polymerization solvent. The quantities of these components in wt. % for the various polymer preparations are shown in the table. While the reaction medium is heated to the target polymerization temperature, the reactor is purged with nitrogen for at least half an hour. As the reactor temperature reaches the set polymerization temperature, typically at about 67° C., the initiator solution 2,2'-azobis(2-methylbutyronitrile) (0.12 wt. % based on the dry weight of the polymer) is injected into the reaction kettle to start the polymerization. The polymerization reaction is continued for at least 6 hours at 67° C. before a series of shots of additional initiator solution are injected into the reactor to remove residual monomers. The total polymer solids in the final dispersion is typically at about 30 wt. %. Upon the completion of the reaction, the polymerization solvent is removed by rotary evaporator under vacuum to recover a polymer powder, which is gently milled to a finer powdered product.

TABLE 1

| Example No. | NVP (wt. %)[1] | VA (wt. %)[1] | SMA (wt. %)[1] | BEM | VA-10 (wt. %)[1] | APE (wt. %)[2] | Stabilizer[3] (wt. %)[2] | PGS[4] (wt. %)[2] | CYCLO (wt. %)[2] | EA (wt. %)[2] |
|---|---|---|---|---|---|---|---|---|---|---|
| 1 | 60 | 40 | — | — | — | 0.1 | 5 | — | 233 | — |
| 2 | 5.41 | 39.60 | 0.99 | — | — | — | 6 | 3.12 | 163.1 | 69.9 |
| 3 | 63.73 | 34.31 | 0.98 | 0.98 | — | 0.15 | 6 | 3.12 | 163.1 | 69.9 |
| 4 | 70 | 30 | — | — | — | 0.1 | 5 | — | 233 | — |
| 5 | 80 | 20 | — | — | — | 0.1 | 5 | — | 233 | — |
| 6 | 84.16 | 14.85 | — | — | 0.99 | — | 5 | 3.12 | 233 | — |
| 7 | 81.73 | 14.42 | 0.96 | 2.88 | — | 0.12 | 6 | 3.12 | 163.1 | 69.9 |
| 8 | 90 | 10 | — | — | — | 0.1 | 5 | — | 233 | — |
| 9 | 82.52 | 14.56 | — | 2.91 | — | 0.12 | 6 | 3.12 | 163.1 | 69.9 |

[1]Based on the weight of the total monomers

[2]Based on the weight of the dry polymer

[3]50/30/20 (wt. %) copolymer of N-vinyl pyrrolidone/stearyl methacrylate/butyl methacrylate utilized as a dispersion polymerization stabilizer

[4]Reaction product $C_{20}$-$C_{24}$ substituted succinic anhydride and glycerin and or polyglycerol containing 2 to 6 glycerin units utilized as a process aid

Example 10

Two-in-one conditioning shampoos containing the cross-linked, nonionic, amphiphilic polymers prepared in accordance with Examples 1-8 are formulated with the components set forth in Table 2.

TABLE 2

| Component | Amount Active (wt. %) |
|---|---|
| PART A | |
| D.I. Water | q.s. to 100 |
| Powdered Dispersion Polymer | Table 3 |
| Sulfochem ™ ES-2 CWK anionic surfactant | 14 |
| Chembetaine ™ C amphoteric surfactant | 3 |
| PART B | |
| Jaguar ® C13-S cationic guar deposition aid | 0.25 |
| PART C | |
| Dow Corning ® silicone emulsion (DC 2-1352) | 2 |
| Glydant ® Plus preservative | 0.22 |
| PART D | 0.25 |
| NaOH (18% aqueous wt./wt.) pH adjusting agent | q.s. to pH 6 |

The shampoo compositions are prepared in accordance with the following procedure:

Part A:
1) Homogeneously disperse the polymer in D.I. water;
2) Add anionic and amphoteric surfactants and mix for 15 min.

Part B:
3) Prepare a 2 wt. % (wt./wt.) dispersion of cationic guar in D.I. water and mix with Part A components.

Part C:
4) Add Part C components to Part AB component mixture and mix until homogeneous;
4) If required, adjust the pH of the ABC component mixture with NaOH to a pH of about 6.

The Brookfield viscosity (BV) and yield stress value of each shampoo formulation is measured in accordance with the test methodology mentioned above. The results are reported in Table 3 below.

TABLE 3

| Polymer Ex. No. | Polymer (wt. %) | BV Viscosity (mPa · s) | Yield Stress (Pa) |
|---|---|---|---|
| 1 | 3.0 | 8280 | 5.0 |
| 2 | 3.0 | 5160 | 3.5 |
| 3 | 2.5 | — | 3.5 |
| 3 | 2.5 | 7580 | 3.2 |
| 4 | 3.0 | 5280 | 4.0 |
| 5 | 3.0 | 3780 | 1.3 |
| 6 | 3.0 | 1250 | 0.4 |
| 7 | 2.5 | 4250 | 2.5 |
| 8 | 3.0 | 3810 | 4.4 |

Examples 11-14

Two-in-one conditioning shampoo containing the cross-linked, nonionic, amphiphilic polymer containing the polymer of Example 9 are prepared in accordance with the method set forth in Example 10 utilizing the components and amounts presented in Table 4. Identical comparative shampoo compositions are similarly formulated with a commercially available Carbomer rheology modifier. Carbomer was chosen as a benchmark as it is widely used to provide rheology and prevent silicone creaming in commercial shampoo formulations (see U.S. Pat. Appln. Pub. No. 2013/0039875; U.S. Pat. No. 5,034,218; European Pat. Appln. No. 0 463 780; and European Pat. No. 0 951 277 B1). A level of 0.4 wt. % Carbomer was chosen, as it is known in the art, and from the preceding disclosures, that this concentration can prevent silicone creaming in a shampoo formulation. The formulations are analyzed on the SITA Foam Tester to determine the amount of foam generated in accordance with the foam volume test methodology described above under test methods. The results are reported in Table 5.

TABLE 4

| Component | Ex. 11 (Active wt. %) | Ex. 12[1] (Active wt. %) | Ex. 13 (Active wt. %) | Ex. 14[1] (Active wt. %) |
|---|---|---|---|---|
| PART A | | | | |
| D.I. Water | q.s. to 100 | q.s. to 100 | q.s. to 100 | q.s. to 100 |
| Polymer of Example 9 | 2.5 | — | 2.5 | — |
| Carbopol ® 980 Carbomer | — | 0.4 | — | 0.4 |
| Sulfochem ™ ALS anionic surfactant | 6 | 6 | 3 | 3 |
| Chembetaine ™ CAD amphoteric surfactant | 1 | 1 | 0.5 | 0.5 |
| PART B | | | | |
| Jaguar ® C13-S cationic guar deposition aid | 0.25 | 0.25 | 0.25 | 0.25 |
| PART C | | | | |
| Dow Corning ® silicone emulsion (DC 2-1352) | 2 | 2 | 2 | 2 |
| Glydant ® Plus preservative | 0.2 | 0.2 | 0.2 | 0.2 |
| PART D | | | | |
| NaOH (18% aqueous wt./wt.) pH adjusting agent | pH 6[2] | q.s. to pH 6 | pH 6[2] | q.s. to pH 6 |

[1]Comparatvie Example
[2]No pH adjustment necessary

TABLE 5

| Ex. No. | Final Foam Volume (mL) | Foam Volume Improvement (%) | Yield Stress (Pa) |
|---|---|---|---|
| 11 | 301 | 51.9 | 3.80 |
| 12[1] | 201 | | 0.13 |
| 13 | 120 | 43.3 | 9.53 |
| 14[1] | 79 | | 2.68 |

[1]Comparative Example

As shown in Table 5 above, the cleansing compositions that include the crosslinked, nonionic, amphiphilic polymers of the invention generate significantly more foam volumes than similarly formulated compositions containing the benchmark Carbomer. The shampoo compositions of Examples 11 and 13 containing the polymers of the invention generate significantly more foam volume when compared to the shampoo compositions of Comparative Examples 12 and 14 formulated with Carbomer.

What is claimed is:

1. A use of a nonionic, amphiphilic polymer to improve the foam properties of an anionic surfactant containing composition comprising the step of incorporating said polymer into said anionic surfactant containing composition, wherein said polymer is prepared from a free radically polymerizable monomer mixture comprising:
    a) from about 55 to about 95 wt. % of at least one vinyl amide monomer (based on the weight of the total monomers present);
    b) from about 5 to about 45 wt. % of at least one vinyl ester of an aliphatic carboxylic acid containing an acyl moiety having 2 to 22 carbon atoms (based on the weight of the total monomers present);
    c) from about 0.01 to about 1 wt. % of at least one polyunsaturated crosslinking monomer containing at least two polymerizable ethylenically unsaturated moieties (based on the total dry weight of the polymer);
    d) from 0 to about 10 wt. % of at least one $C_1$-$C_{22}$ alkyl (meth)acrylate (based on the weight of the total monomers present);
    e) from 0 to about 10 wt. % of an alkoxylated associative monomer (based on the weight of the total monomers present);
    f) from 0 to about 10 wt. % of an alkoxylated semi-hydrophobic monomer (based on the weight of the total monomers present); and
    g) from 0 to about 5 wt. % of at least one vinyl ester of an aliphatic carboxylic acid containing an acyl moiety having 2 to 22 carbon atoms (based on the weight of the total monomers present) other than vinyl acetate.

2. A use according to claim 1, wherein said monomer composition further comprises from about 0.01 to about 15 wt. % of at least one copolymerizable monomer selected from:
    h) at least one $C_1$-$C_5$ hydroxyalkyl (meth)acrylate;
    i) at least one (meth)acrylamide selected from (meth)acrylamide, N—($C_1$-$C_5$)alkyl (meth)acrylamide, N,N-di($C_1$-$C_5$)alkyl (meth)acrylamide, N—($C_1$-$C_5$)alkylamino($C_1$-$C_5$)alkyl(meth)acrylamide or N,N-di($C_1$-$C_5$)alkylamino($C_1$-$C_5$)alkyl(meth)acrylamide;
    j) at least one alpha-olefinic monomer; and mixtures thereof.

3. A use according to claim 1, wherein said at least one vinyl amide is selected from N-vinylformamide, N-methyl-N-vinylformamide, N-(hydroxymethyl)-N-vinylformamide, N-vinyl acetamide, N-vinylmethylacetamide, N-(hydroxymethyl)-N-vinylacetamide, and mixtures thereof and cyclic N-vinyl amides selected from N-vinyl-2-pyrrolidinone, N-(1-methyl vinyl) pyrrolidinone, N-vinyl-2-piperidone, N-vinyl-2-caprolactam, N-vinyl-5-methyl pyrrolidinone, N-vinyl-3,3-dimethyl pyrrolidinone, N-vinyl-5-ethyl pyrrolidinone and N-vinyl-6-methyl piperidone, and mixtures thereof.

4. A use according to claim 1, wherein said at least one vinyl ester of an aliphatic carboxylic acid containing an acyl moiety having 2 to 22 carbon atoms is selected from vinyl acetate, vinyl propionate, vinyl butyrate, vinyl isobutyrate, vinyl valerate, vinyl hexanoate, vinyl 2-methylhexanate, vinyl 2-ethylhexanoate, vinyl iso-octanoate, vinyl nonanoate, vinyl neodecanoate, vinyl decanoate, vinyl versatate, vinyl laurate, vinyl palmitate, vinyl stearate, and mixtures thereof.

5. A use according to claim 1, wherein the at least one polyunsaturated crosslinking monomer is selected from a monomer having an average of 2 crosslinkable unsaturated functional groups, an average of 3 crosslinkable unsaturated functional groups, and mixtures thereof.

6. A use according to claim 2, wherein said $C_1$-$C_5$ hydroxyalkyl (meth)acrylate monomer is selected from 2-hydroxyethyl(meth)acrylate, 3-hydroxypropyl(meth)acrylate, 4-hydroxybutyl(meth)acrylate, and mixtures thereof.

7. A use according to claim 5, wherein the at least one crosslinking monomer is selected from polyallyl ethers of trimethylolpropane, polyallyl ethers of pentaerythritol, polyallyl ethers of sucrose, and mixtures thereof.

8. A use according to claim 1, wherein said at least one $C_1$-$C_{22}$ alkyl (meth)acrylate is selected from methyl (meth)acrylate, ethyl (meth)acrylate butyl (meth)acrylate, sec-butyl (meth)acrylate, iso-butyl (meth)acrylate, hexyl (meth)acrylate), heptyl (meth)acrylate, octyl (meth)acrylate, 2-ethylhexyl (meth)acrylate, decyl (meth)acrylate, isodecyl (meth)acrylate, lauryl (meth)acrylate, tetradecyl (meth)acrylate, hexadecyl (meth)acrylate, stearyl (meth)acrylate, behenyl (meth)acrylate, and mixtures thereof.

9. A use according to claim 1, wherein said associative monomer comprises (i) a polymerizable ethylenically unsaturated end group portion, (ii) a polyoxyalkylene midsection portion, and (iii) a hydrophobic end group portion containing 7 to 30 carbon atoms.

10. A use according to claim 9, wherein said associative monomer is represented by formulas VII and/or VIIA:

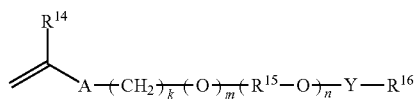

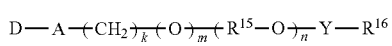

wherein $R^{14}$ is hydrogen or methyl; A is —$CH_2$C(O)O—, —C(O)O—, —O—, —$CH_2$O—, —NHC(O)NH—, —C(O)NH—, —Ar—($CE_2$)$_z$-NHC(O)O—, —Ar—($CE_2$)$_z$-NHC(O)NH—, or —$CH_2CH_2$NHC(O)—; a divalent alkylene radical containing 1 to 5 carbon atoms; Ar is a divalent arylene; E is H or methyl; z is 0 or 1; k is an integer ranging from 0 to about 30, and m is 0 or 1, with the proviso that when k is 0, m is 0, and when k is in the range of 1 to about 30, m is 1; D represents a vinyl or an allyl moiety; ($R^{15}$—O)$_n$ is a polyoxyalkylene moiety, which can be a homopolymer, a random copolymer, or a block copolymer of $C_2$-$C_4$ oxyalkylene units, $R^{15}$ is a divalent alkylene moiety selected from $C_2H_4$, $C_3H_6$, or $C_4H_8$, and combinations thereof; and n is an integer in the range of about 2 to about 150; Y is —$R^{15}$O—, —$R^{15}$NH—, —C(O)—, —C(O)NH—, —$R^{15}$NHC(O)NH—, or —C(O)NHC(O)—; $R^{16}$ is a substituted or unsubstituted alkyl selected from a $C_8$-$C_{30}$ linear alkyl, a $C_8$-$C_{30}$ branched alkyl, a $C_7$-$C_{30}$ carbocyclic alkyl, a $C_2$-$C_{30}$ alkyl-substituted phenyl, an araalkyl substituted phenyl, and an aryl-substituted $C_2$-$C_{30}$ alkyl; wherein the $R^{16}$ alkyl group, carbocyclic alkyl group, aryl group, phenyl group optionally comprises one or more substituents selected from the group selected from a methyl group, hydroxyl group, an alkoxyl group, benzyl group styryl group, and a halogen group.

11. A use according to claim 10, wherein said associative monomer is represented by formula VIIB:

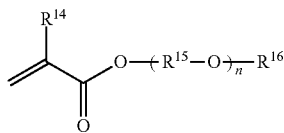

VIIB wherein $R^{14}$ is hydrogen or methyl; $R^{15}$ is a divalent alkylene moiety independently selected from $C_2H_4$, $C_3H_6$, and $C_4H_8$, and n represents an integer ranging from about 10 to about 60, ($R^{15}$—O) can be arranged in a random or a block configuration; $R^{16}$ is a substituted or unsubstituted alkyl selected from a $C_8$-$C_{30}$ linear alkyl, a $C_8$-$C_{30}$ branched alkyl, a $C_7$-$C_{30}$ carbocyclic alkyl, a $C_2$-$C_{30}$ alkyl-substituted phenyl, an araalkyl substituted phenyl, and an aryl-substituted $C_2$-$C_{30}$ alkyl, wherein the $R^{16}$ alkyl group, aryl group, phenyl group optionally comprises one or more substituents selected from the group consisting of a hydroxyl group, an alkoxyl group, benzyl group styryl group, and a halogen group.

12. A use according to claim 1, wherein said semi-hydrophobic monomer comprises (i) a polymerizable ethylenically unsaturated end group portion, (ii) a polyoxyalkylene mid-section portion, and (iii) an end group portion selected from hydrogen or an alkyl group containing 1 to 4 carbon atoms.

13. A use according to claim 12, wherein said semi-hydrophobic monomer is selected from at least one monomer represented by formulas VIII and IX:

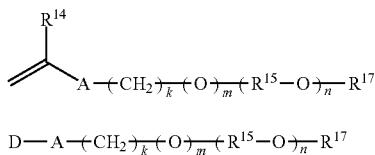

VIII

IX wherein $R^{14}$ is hydrogen or methyl; A is —$CH_2C(O)O$—, —C(O)O—, —O—, —$CH_2O$—, —NHC(O)NH—, —C(O)NH—, —Ar—$(CE_2)_z$-NHC(O)O—, —Ar—$(CE_2)_z$-NHC(O)NH—, or —$CH_2CH_2NHC(O)$—; Ar is a divalent arylene; E is H or methyl; z is 0 or 1; k is an integer ranging from 0 to about 30, and m is 0 or 1, with the proviso that when k is 0, m is 0, and when k is in the range of 1 to about 30, m is 1; ($R^{15}$—O)$_n$ is a polyoxyalkylene moiety, which can be a homopolymer, a random copolymer, or a block copolymer of $C_2$-$C_4$ oxyalkylene units, $R^{15}$ is a divalent alkylene moiety selected from $C_2H_4$, $C_3H_6$, or $C_4H_8$, and combinations thereof; and n is an integer in the range of about 2 to about 150; $R^{17}$ is selected from hydrogen and a linear or branched $C_1$-$C_4$ alkyl group; and D represents a vinyl or an allyl moiety.

14. A use according to claim 13, wherein said semi-hydrophobic monomer is selected from at least one monomer represented by formulas VIIIA and VIIIB:

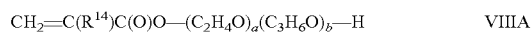    VIIIA

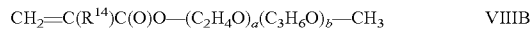    VIIIB wherein $R^{14}$ is hydrogen or methyl, and "a" is an integer ranging from 0 to about 120, and "b" is an integer ranging from 0 to about 120, subject to the proviso that "a" and "b" cannot be 0 at the same time.

15. A use according to claim 2, wherein said at least one (meth)acrylamide is selected from N-methyl(meth)acryl amide, N-ethyl(meth)acryl amide, N-propyl(meth)acrylamide, N-isopropyl(meth)acrylamide, N-tert-butyl(meth)acrylamide, N-tert-octyl(meth)acrylamide, N-(2-hydroxyethyl)(meth)acrylamide, N-(3-hydroxypropyl)(meth)acrylamide; N,N-dimethyl(meth)acryl amide, N,N-diethyl(meth)acryl amide, N,N-(di-2-hydroxyethyl)(meth)acryl amide, N,N-(di-3-hydroxypropyl)(meth)acrylamide, N-methyl,N-ethyl(meth)acrylamide; N,N-dimethylaminoethyl(meth)acryl amide, N,N-diethylaminoethyl(meth)acrylamide, N,N-dimethylaminopropyl(meth)acrylamide; and mixtures thereof.

16. A use according to claim 10, wherein said at least one associative monomer is selected from lauryl polyethoxylated (meth)acrylate (LEM), cetyl polyethoxylated (meth)acrylate (CEM), cetearyl polyethoxylated (meth)acrylate (C SEM), stearyl polyethoxylated (meth)acrylate, arachidyl polyethoxylated (meth)acrylate, behenyl polyethoxylated (meth)acrylate (BEM), cerotyl polyethoxylated (meth)acrylate, montanyl polyethoxylated (meth)acrylate, melissyl polyethoxylated (meth)acrylate, phenyl polyethoxylated (meth)acrylate, nonylphenyl polyethoxylated (meth)acrylate, ω-tristyrylphenyl polyoxyethylene (meth)acrylate, where the polyethoxylated portion of the monomer contains from about 2 to about 150 ethylene oxide units; octyloxy polyethyleneglycol polypropyleneglycol (meth)acrylate, phenoxy polyethylene glycol polypropylene glycol (meth) acrylate, and nonylphenoxy polyethylene glycol polypropylene glycol (meth)acrylate, where the polyethoxylated and/or the polypropoxylated portion of the monomer independently contain 0 to about 120; and mixtures thereof.

17. A use according to claim 14, wherein said at least one semi-hydrophobic monomer is selected from polyethyleneglycol (meth)acrylate, polypropyleneglycol (meth)acrylate, polyethyleneglycol polypropylene glycol methacrylate or methoxypolyethyleneglycol (meth)acrylate, where the polyethoxylated and/or the polypropoxylated portion of the monomer independently contain 0 to about 120; and
  mixtures thereof.

18. A use according to claim 13, wherein said at least one semi-hydrophobic monomer is selected from a compound having the formula: $CH_2$=CH—O$(CH_2)_4$O$(C_3H_6O)_4$$(C_2H_4O)_{10}$H; $CH_2$=CH—O$(CH_2)_4$O$(C_3H_6O)_4$$(C_2H_4O)_{20}$H; $CH_2$=CH—O$(CH_2)_4$O$(C_3H_6O)_4$$(C_2H_4O)_{30}$H; $CH_2$=CHCH$_2$O$(C_3H_6O)_4$$(C_2H_4O)_{10}$H; $CH_2$=CHCH$_2$O$(C_3H_6O)_4$$(C_2H_4O)_{20}$H; $CH_2$=CHCH$_2$O$(C_3H_6O)_4$$(C_2H_4O)_{30}$H; and $CH_2$=CHCH$_2$O$(C_3H_6O)_5$$(C_2H_4O)_5$H.

19. A use according to claim 2, wherein said at least one alpha-olefinic monomer is selected from ethylene, propylene, 1-butene, iso-butylene, 1-hexene, 1-heptene, 4-methyl-1-pentene, styrene, alpha-methyl styrene, and mixtures thereof.

20. A use according to claim 1, wherein said nonionic, amphiphilic polymer comprises repeating units prepared from a monomer mixture comprising:
   a) from about 55 to about 95 wt. % of N-vinyl pyrrolidone (based on the weight of the total monomers present);
   b) from about 5 to about 45 wt. % of vinyl acetate (based on the weight of the total monomers present);
   c) from about 0.01 to about 1 wt. % of at least one polyunsaturated crosslinking monomer containing at least two polymerizable ethylenically unsaturated moieties (based on the total dry wt. of the polymer);
   d) from 0 to about 10 wt. % (based on the weight of the total monomers present) of at least one $C_1$-$C_{22}$ alkyl (meth)acrylate selected from methyl (meth)acrylate, butyl (meth)acrylate, sec-butyl (meth)acrylate, iso-butyl (meth)acrylate, hexyl (meth)acrylate), heptyl (meth) acrylate, octyl (meth)acrylate, 2-ethylhexyl (meth) acrylate, decyl (meth)acrylate, isodecyl (meth)acrylate, lauryl (meth)acrylate, tetradecyl (meth)acrylate, hexadecyl (meth)acrylate, stearyl (meth)acrylate, or behenyl (meth)acrylate; and
   e) from 0 to about 10 wt. % (based on the weight of the total monomers present), of an alkoxylated associative monomer selected from lauryl polyethoxylated (meth)acrylate, cetyl polyethoxylated (meth)acrylate, cetearyl polyethoxylated (meth)acrylate, stearyl polyethoxylated (meth)acrylate, arachidyl polyethoxylated (meth)acrylate, behenyl polyethoxylated (meth)acrylate, cerotyl polyethoxylated (meth)acrylate, montanyl polyethoxylated (meth)acrylate, melissyl polyethoxylated (meth)acrylate, phenyl polyethoxylated (meth)acrylate, nonylphenyl polyethoxylated (meth)acrylate, co-tristyrylphenyl polyoxyethylene methacrylate, where the polyethoxylated portion of the monomer contains from about 2 to about 150 ethylene oxide units.

21. A use according to claim 20, wherein said nonionic, amphiphilic polymer comprises repeating units prepared from a monomer mixture further comprising from about 0.5 to about 5 wt. % (based on the weight of the total monomers present) of a vinyl ester of an aliphatic carboxylic acid containing an acyl moiety having 2 to 22 carbon atoms other than vinyl acetate selected from vinyl propionate, vinyl butyrate, vinyl isobutyrate, vinyl valerate, vinyl hexanoate, vinyl 2-methylhexanate, vinyl 2-ethylhexanoate, vinyl iso-octanoate, vinyl nonanoate, vinyl neodecanoate, vinyl decanoate, vinyl versatate, vinyl laurate, vinyl palmitate, and vinyl stearate.

22. A use according to claim 20, wherein said $C_1$-$C_{22}$ alkyl (meth)acrylate is stearyl methacrylate.

23. A use according to claim 20 wherein said-alkoxylated associative monomer is behenyl polyethoxylated methacrylate.

24. A use according to claim 20, wherein said the at least one crosslinking monomer is selected from trimethylolpropane tri(meth)acrylate, trimethylolethane tri(meth)acrylate, tetramethylolmethane tri(meth)acrylate, and mixtures thereof.

25. A use according to claim 20, wherein said at least one crosslinking monomer is selected from pentaerythritol diallyl ether, pentaerythritol triallyl ether, pentaerythritol tetraallyl ether; and mixtures thereof.

26. A use according to claim 1, wherein said surfactant composition further comprises at least one amphoteric surfactant.

27. A use according to claim 1, wherein the at least one anionic surfactant is ethoxylated.

28. A use according to claim 27, wherein the at least one anionic surfactant contains an average of 1 to 3 moles of ethoxylation.

29. A use according to claim 1, wherein the at least one anionic surfactant is selected from sodium dodecyl sulfate, ammonium dodecyl sulfate, sodium lauryl sulfate, sodium trideceth sulfate, ammonium lauryl sulfate, sodium laureth sulfate, ammonium laureth sulfate or mixtures thereof.

30. A use according to claim 26, wherein the at least one amphoteric surfactant is selected from amino acid surfactants, betaines, sultaines, alkyl amphocarboxylates, and mixtures thereof.

31. A use according to claim 30, wherein the at least one amphoteric surfactant is cocamidopropyl betaine.

32. A use according to claim 1, wherein the concentration of the at least one anionic surfactant ranges from about 1 or 3 to about 22 wt. % (active), based on the weight of the total composition.

33. A use according to claim 30, wherein the ratio of anionic surfactant to amphoteric surfactant (active) is about 10:1 to about 2:1.

34. A use according to claim 1, wherein the amount of nonionic, amphiphilic polymer solids in said composition ranges from about 1 to about 3 wt. %, based on the weight of the total composition.

35. A use according to claim 1, wherein said monomer mixture further comprises a steric stabilizer.

36. A use according to claim 35, wherein said monomer mixture further comprises a steric stabilizer selected from a copolymer of N-vinyl pyrrolidone/stearyl methacrylate/butyl acrylate, the ester of the reaction product of a $C_{20}$ to $C_{24}$ alkyl substituted succinic anhydride and a polyol selected from glycerin and/or a polyglycerol containing 2 to 6 glycerin units, and mixtures thereof.

37. A use according to claim 1 wherein said nonionic, amphiphilic polymer is a dispersion polymer.

38. A use of from about 1 to about 5 wt. % of a nonionic, amphiphilic dispersion polymer for improving the foam properties of an anionic surfactant containing composition comprising the step of incorporating said polymer into said anionic surfactant containing composition, wherein said polymer is prepared from a monomer mixture comprising:
   a) from about 55 to about 95 wt. % of N-vinyl pyrrolidone (based on the weight of the total monomers present);
   b) from about 5 to about 45 wt. % of vinyl acetate (based on the weight of the total monomers present);
   c) from 0 to about 1 wt. % of at least one polyunsaturated crosslinking monomer containing at least two polymerizable ethylenically unsaturated moieties (based on the total dry wt. of the polymer);
   d) from 0 to about 10 wt. % (based on the weight of the total monomers present), of at least one $C_1$-$C_{22}$ alkyl (meth)acrylate selected from methyl (meth)acrylate, butyl (meth)acrylate, sec-butyl (meth)acrylate, iso-butyl (meth)acrylate, hexyl (meth)acrylate), heptyl (meth) acrylate, octyl (meth)acrylate, 2-ethylhexyl (meth) acrylate, decyl (meth)acrylate, isodecyl (meth)acrylate, lauryl (meth)acrylate, tetradecyl (meth)acrylate, hexadecyl (meth)acrylate, stearyl (meth)acrylate, or behenyl (meth)acrylate; and
   e) from about 0.5 to about 10 wt. % (based on the weight of the total monomers present) of an alkoxylated associative monomer selected from lauryl polyethoxylated (meth)acrylate, cetyl polyethoxylated (meth)acrylate, cetearyl polyethoxylated (meth)acrylate, stearyl polyethoxylated (meth)acrylate, arachidyl polyethoxylated (meth)acrylate, behenyl polyethoxylated (meth)acrylate, cerotyl polyethoxylated (meth)acrylate, montanyl polyethoxylated (meth)acrylate, melissyl polyethoxylated (meth)acrylate, phenyl polyethoxylated (meth)acrylate, nonylphenyl polyethoxylated (meth)acrylate, co-tristyrylphenyl polyoxyethylene methacrylate, where the polyethoxylated portion of the monomer contains from about 2 to about 150 ethylene oxide units;

f) from 0 to about 10 wt. % (based on the weight of the total monomers present) of a semi-hydrophobic monomer selected from methoxy polyethyleneglycol methacrylate;

g) from 0 to about 10 wt. % (based on the weight of the total monomers present) of at least one vinyl ester of an aliphatic carboxylic acid containing an acyl moiety having 2 to 22 carbon atoms other than vinyl acetate selected from vinyl propionate, vinyl butyrate, vinyl isobutyrate, vinyl valerate, vinyl hexanoate, vinyl 2-methylhexanate, vinyl 2-ethylhexanoate, vinyl iso-octanoate, vinyl nonanoate, vinyl neodecanoate, vinyl decanoate, vinyl versatate, vinyl laurate, vinyl palmitate, and vinyl stearate.

39. A use according to claim 38, wherein said monomer mixture further comprises a steric stabilizer selected from a copolymer of N-vinyl pyrrolidone/stearyl methacrylate/butyl acrylate, the ester of the reaction product of a $C_{20}$ to $C_{24}$ alkyl substituted succinic anhydride and a polyol selected from glycerin and/or a polyglycerol containing 2 to 6 glycerin units, and mixtures thereof.

40. A use according to claim 38, wherein said monomer mixture comprises:
   a) 55 to about 95 wt. %, of N-vinyl pyrrolidone (based on the weight of the total monomers present);
   b) from about 5 to about 45 wt. % of vinyl acetate (based on the weight of the total monomers present);
   c) from 0 to about 1 wt. % of at least one polyunsaturated crosslinking monomer containing at least two polymerizable ethylenically unsaturated moieties (based on the total dry wt. of the polymer);
   d) from 0 to about 5 wt. % (based on the weight of the total monomers present) of at least one monomer selected from decyl (meth)acrylate, isodecyl (meth)acrylate, lauryl (meth)acrylate, tetradecyl (meth)acrylate, hexadecyl (meth)acrylate, stearyl (meth)acrylate, or behenyl (meth)acrylate;
   e) from 0 to about 5 wt. % (based on the weight of the total monomers present) of an alkoxylated associative monomer selected from lauryl polyethoxylated (meth)acrylate, cetyl polyethoxylated (meth)acrylate, cetearyl polyethoxylated (meth)acrylate, stearyl polyethoxylated (meth)acrylate, behenyl polyethoxylated (meth)acrylate, where the polyethoxylated portion of the monomer contains from about 10 to about 60 ethylene oxide units;
   f) from 0 to about 5 wt. % (based on the weight of the total monomers present) of a semi-hydrophobic monomer selected from methoxy polyethyleneglycol methacrylate; and
   g) from 0 to about 5 wt. %, (based on the weight of the total monomers present) of at least one vinyl ester of an aliphatic carboxylic acid containing an acyl moiety having 2 to 22 carbon atoms other than vinyl acetate selected from vinyl propionate, vinyl butyrate, vinyl isobutyrate, vinyl valerate, vinyl hexanoate, vinyl 2-methylhexanate, vinyl 2-ethylhexanoate, vinyl iso-octanoate, vinyl nonanoate, vinyl neodecanoate, vinyl decanoate, vinyl versatate, vinyl laurate, vinyl palmitate, and vinyl stearate.

41. A use according to claim 38, wherein said surfactant containing composition further comprises an amphoteric surfactant and the ratio of said anionic surfactant to said amphoteric surfactant ranges from about 10:1 to about 2:1 (wt./wt.).

42. A use according to claim 41, wherein said anionic surfactant is selected from the sodium or ammonium salts of dodecyl sulfate, lauryl sulfate, laureth sulfate, or mixtures thereof.

43. A use according to claim 42, wherein said amphoteric surfactant is cocamidopropyl betaine.

44. A use according to claim 38, further comprising a non-volatile silicone conditioning agent selected from a silicone oil, silicone gum, silicone resin, and mixtures thereof.

45. A use according to claim 38, further comprising a volatile silicone.

46. A use according to claim 44 wherein said silicone oil is selected from a compound represented by the formula:

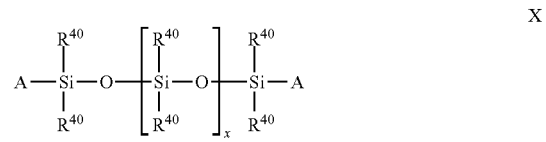

X wherein A independently represents hydroxy, methyl, methoxy, ethoxy, propoxy, and phenoxy; $R^{40}$ independently represents methyl, ethyl, propyl, phenyl, methylphenyl, phenylmethyl; and x is an integer ranging from about 7 to about 8000.

47. A use according to claim 44, wherein said silicone conditioning agent is selected from polydimethylsiloxanes (dimethicones), polydiethylsiloxanes, polydimethyl siloxanes having terminal hydroxyl groups (dimethiconols), polymethylphenylsiloxanes, phenylmethylsiloxanes, and mixtures thereof.

48. A use according to claim 44, wherein said silicone conditioning agent is selected from an amino functional polydimethylsiloxane.

49. A use according to claim 48, wherein said amino functional silicone is selected from a compound represented by the formula:

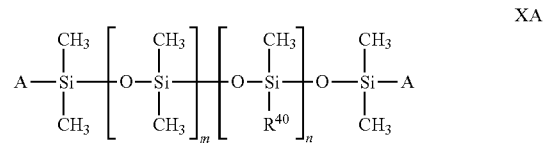

XA wherein A independently represents hydroxy, methyl, methoxy, ethoxy, propoxy, and phenoxy; and $R^{40}$ is selected from:
—$R^{41}$—$N(R^{42})CH_2CH_2N(R^{42})_2$;
—$R^{41}$—$N(R^{42})_2$;
—$R^{41}$—$N^+(R^{42})_3CA^-$; and
—$R^{41}$—$N(R^{42})CH_2CH_2N(R^{42})H_2CA^-$ wherein $R^{41}$ is a linear or branched, hydroxyl substituted or unsubstituted alkylene or alkylene ether moiety containing 2 to 10 carbon atoms; $R^{42}$ is hydrogen, $C_1$-$C_{20}$ alkyl, phenyl or benzyl; $CA^-$ is a halide ion selected from chlorine, bromine, iodine and fluorine; and the sum of m+n ranges from about 7 to about 1000, subject to the proviso that m or n is not 0.

50. A use according to claim 44, wherein said silicone conditioning agent is present in an amount ranging from about 0.01 to about 20 wt. % based on the weight of the total composition.

51. A use according to claim 44, wherein said silicone conditioning agent has a particle size ranging from about 0.003 to about 500 μm.

52. A use according to claim 44, wherein said silicone conditioning agent is in the form of emulsion droplets.

53. A use according to claim 44, further comprising an auxiliary conditioning agent selected from a hydrocarbon oil, an ester oil, and combinations thereof.

54. A use according to claim 44, further comprising a cationic polymer.

55. A use according to claim 44, further comprising a pearlizing agent.

56. A use according to claim 55, wherein said pearlizing agent is selected from mica, metal oxide coated mica, silica coated mica, bismuth oxychloride coated mica, bismuth oxychloride, myristyl myristate, glass, metal oxide coated glass, various aluminum and magnesium salts, guanine, fish scales, glitter, and mixtures thereof.

57. A use according to claim 55, wherein said pearlizing agent is selected from monoesters and/or diesters of ethylene glycol, propylene glycol, diethylene glycol, dipropylene glycol, triethylene glycol and tetraethylene glycol with fatty acids containing from about 6 to about 22 carbon atoms.

58. A use according to claim 57, wherein said pearlizing agent is selected from ethylene glycol monostearate (EGMS), ethylene glycol distearate (EGDS), polyethylene glycol monostearate (PGMS), polyethyleneglycol distearate (PGDS), and mixtures thereof.

59. A use according to claim 44, further comprising a particulate material selected from pigments, exfoliating agents, anti-dandruff agents, clay, swellable clay, laponite, gas bubbles, liposomes, UV absorbers, antibacterial compositions, hair fixative, anti-wrinkling and anti-aging compositions, microsponges, cosmetic beads and flakes.

60. A use according to claim 44, wherein said composition is able to suspend beads of a size between 0.5 and 1.5 mm for at least one month at 23° C. wherein the difference in specific gravity between the bead material and water is between +/−0.01 and 0.5.

61. A use according to claim 40, wherein said composition is selected from shampoos, baby shampoos, body washes, shower gels, liquid hand soaps, liquid dishwashing detergents, pet cleansing product, moist cleansing wipes, or facial cleansers.

* * * * *